US008674069B2

(12) United States Patent
Tsunoda et al.

(10) Patent No.: US 8,674,069 B2
(45) Date of Patent: Mar. 18, 2014

(54) MELK EPITOPE PEPTIDES AND VACCINES CONTAINING THE SAME

(75) Inventors: Takuya Tsunoda, Kanagawa (JP); Ryuji Ohsawa, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 204 days.

(21) Appl. No.: 13/056,598

(22) PCT Filed: Jul. 30, 2009

(86) PCT No.: PCT/JP2009/003630
§ 371 (c)(1),
(2), (4) Date: May 23, 2011

(87) PCT Pub. No.: WO2010/013485
PCT Pub. Date: Feb. 4, 2010

(65) Prior Publication Data
US 2011/0212115 A1    Sep. 1, 2011

Related U.S. Application Data

(60) Provisional application No. 61/085,663, filed on Aug. 1, 2008.

(51) Int. Cl.
C07K 5/00    (2006.01)

(52) U.S. Cl.
USPC .......................... 530/326; 530/327; 530/328

(58) Field of Classification Search
None
See application file for complete search history.

(56) References Cited

U.S. PATENT DOCUMENTS

| 6,229,001 B1 * | 5/2001 | Barrow et al. ............... 536/23.1 |
| 6,605,709 B1 * | 8/2003 | Breton ......................... 536/23.1 |
| 6,833,447 B1 * | 12/2004 | Goldman et al. ............ 536/23.1 |
| 6,974,867 B2 * | 12/2005 | Wu et al. ..................... 536/24.1 |
| 7,504,111 B2 * | 3/2009 | Fontana et al. ............. 424/249.1 |
| 7,504,120 B2 * | 3/2009 | Steer et al. ...................... 426/63 |
| 8,067,671 B2 * | 11/2011 | Boukharov et al. .......... 800/285 |
| 2002/0049180 A1 | 4/2002 | Wu et al. |
| 2002/0156263 A1 | 10/2002 | Chen |
| 2008/0293044 A1 | 11/2008 | Kadyk et al. |
| 2009/0175844 A1 | 7/2009 | Nakamura et al. |
| 2009/0263395 A1 | 10/2009 | Nakamura et al. |
| 2009/0317392 A1 | 12/2009 | Nakamura et al. |

FOREIGN PATENT DOCUMENTS

| CN | 101160524 A | 4/2008 |
| EP | 1930433 A1 | 6/2008 |
| JP | 2008-509652 A | 4/2008 |
| KR | 1998-0026247 B1 | 7/1999 |
| WO | WO 03/065006 A2 | 8/2003 |
| WO | WO 2004/031413 A2 | 4/2004 |
| WO | WO 2004/070062 A2 | 8/2004 |
| WO | WO 2005/016279 A2 | 2/2005 |
| WO | WO 2005/039382 A2 | 5/2005 |
| WO | WO 2005/073374 A1 | 8/2005 |
| WO | WO 2006/016525 A2 | 2/2006 |
| WO | 2006/091734 A2 | 8/2006 |
| WO | WO 2006/085684 A2 | 8/2006 |
| WO | WO 2007/013665 A2 | 2/2007 |
| WO | WO 2007/032255 A1 | 3/2007 |
| WO | WO 2008/023841 A1 | 2/2008 |
| WO | WO 2010/013485 A1 | 2/2010 |

OTHER PUBLICATIONS

Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Johnson et al, Cancer Treatment Reviews vol. 2p. 1, (1975).*
Sasada, et al., "Identification of HLA-A*0201-restricted cytotoxic T lymphocyte (CTL) epitopes from a novel melanoma antigen, maternal embryonic leucine zipper kinase (MELK)," *Proceedings of the American Association for Cancer Research Annual Meeting*, vol. 49, pp. 1101-1102, 99th AACR Annual Meeting, Apr. 12-16, 2008 San Diego, CA.
Adams, et al., "Prediction of binding to MHC class I molecules," *J Immunol Methods*, vol. 185(2), pp. 181-190 (Sep. 25, 1995).
Bachinsky, et al., "Mapping and binding analysis of peptides derived from the tumor-associated antigen survivin for eight HLA alleles," *Cancer Immun.*, vol. 5:6, 9 pages (Mar. 22, 2005).
Baker, et al., "Suppression of Human Colorectal Carcinoma Cell Growth by Wild-Type p53," *Science*, vol. 249(4971), pp. 912-915 (Aug. 24, 1990).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Blot, et al., "Cell Cycle Regulation of pEg3, a New *Xenopus* Protein Kinase of the KIN1/PAR-1/MARK Family," *Dev Biol.*, vol. 241(2), pp. 327-338 (Jan. 15, 2002).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).

(Continued)

*Primary Examiner* — Sheela J Huff
(74) *Attorney, Agent, or Firm* — Kilpatrick Townsend & Stockton LLP

(57) ABSTRACT

According to the present invention, peptides having the amino acid sequence of SEQ ID NOs: 14, 21, 23, 27, 36, 46, 57, 60 and 62 were demonstrated to have cytotoxic T lymphocyte (CTL) inducibility. Therefore, the present invention provides a peptide having the amino acid sequence selected from among SEQ ID NOs: 14, 21, 23, 27, 36, 46, 57, 60 and 62. The peptide can include one, two, or several amino acid substitutions, deletions, insertions, or additions so long as its CTL inducibility is retained. Furthermore, the present invention provides pharmaceutical agents for the treatment and/or prophylaxis of cancers, and/or prevention of postoperative recurrence thereof, which contain any of these peptides. Pharmaceutical agents of this invention include vaccines.

8 Claims, 4 Drawing Sheets

(56) References Cited

OTHER PUBLICATIONS

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al., "Cytolytic T-cell responses of cancer patients vaccinated with a MAGE antigen," *Immunol Rev.*, vol. 188, pp. 33-42 (Oct. 2002).
Davezac, et al., "Human pEg3 kinase associates with and phosphorylates CDC25B phosphatase: a potential role for pEg3 in cell cycle regulation," *Oncogene*, vol. 21(50), pp. 7630-7641 (Oct. 31, 2002).
Drewes, et al., "The protein kinase kin1, the fission yeast orthologue of mammalian MARK/PAR-1, localises to new cell ends after mitosis and is important for bipolar growth," *FEBS Lett.*, vol. 554(1-2), pp. 45-49 (Nov. 6, 2003).
Fujie, et al., "A *MAGE*-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Gray, et al., "Maternal Embryonic Leucine Zipper Kinase/Murine Protein Serine-Threonine Kinase 38 Is a Promising Therapeutic Target for Multiple Cancers," *Cancer Res.*, vol. 65(21), pp. 9751-9761 (Nov. 1, 2005).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Heyer, et al., "Expression of *Melk*, a New Protein Kinase, During Early Mouse Development," *Dev Dyn.*, vol. 215(4), pp. 344-351 (Aug. 1999).
Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Kuzushima, et al., "Efficient identification of HLA-A *2402-restricted cytomegalovirus-specific $CD8^+$ T-cell epitopes by a computer algorithm and an enzyme-linked immunospot assay," *Blood*, vol. 98(6), pp. 1872-1881 (Sep. 15, 2001).
Lin, et al., "Characterization of novel molecular targets for development of anti-cancer drugs for human breast cancer," *Proceedings of the 63rd Annual Meeting of the Japanese Cancer Association*, Supplement 95, Abstract #W-116, p. 75 (Aug. 25, 2004).
Lin, et al., "Characterization of MMK4 as a novel molecular target for development of anti-cancer drugs for human breast cancer," *Proceedings of the 65th Annual Meeting of the Japanese Cancer Association*, vol. 65, Abstract P-231, p. 155 (2006).
Lin, et al., "MMK4 is a promising therapeutic target for breast cancer," *The American Association for Cancer Research/AACR*, vol. 47, Abstract #4829, p. 1134 (Apr. 2006).
Lin, et al., "Involvement of maternal embryonic leucine zipper kinase (MELK) in mammary carcinogenesis through interaction with Bcl-G, a pro-apoptotic member of the Bcl-2 family," *Breast Cancer Res.*, vol. 9(1), R17, 13 pages (2007).
Morgan, et al., "High Efficiency TCR Gene Transfer into Primary Human Lymphocytes Affords Avid Recognition of Melanoma Tumor Antigen Glycoprotein 100 and Does Not Alter the Recognition of Autologour Melanoma Antigens," *J. Immunol.*, vol. 171(6), pp. 3287-3295 (Sep. 15, 2003).
Nakano, et al., "Molecular characterization of maternal leucine-zipper kinase (MELK) in central nervous system stem/progenitor cells," *Society for Neuroscience*, Abstract Viewer and Itinerary Planner, 124.4, 1 page (2003).
Nakano, et al., "Maternal embryonic leucine zipper kinase (MELK) regulates multipotent neural progenitor proliferation," *J Cell Biol.*, vol. 170(3), pp. 413-427 (Aug. 1, 2005).

Oiso, et al., "A Newly Identified *MAGE-3*-Derived Epitope Recognized by HLA-A24-Restricted Cytotoxic T Lymphocytes," *Int J Cancer*, vol. 81(3), pp. 387-394 (May 5, 1999).
Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Rosenberg, et al., "Cancer immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Seong, et al., "Phosphorylation of a novel zinc-finger-like protein, ZPR9, by a murine protein serine/threonine kinase 38 (MPK38)," *Biochem J.*, vol. 361(Pt 3), pp. 597-604 (Feb. 1, 2002).
Tanaka, et al., "Indcution of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
Tassan, et al., "An overview of the KIN1/PAR-1/MARK kinase family," *Biol Cell*, vol. 96(3), pp. 193-199 (Apr. 2004).
Van Der Burg, et al., "Immunogenicity of Peptides Bound to MHC Class 1 Molecules Depends on the MHC-Peptide Complex Stability," *J. Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).
Vulsteke, et al., "Inhibition of Spliceosome Assembly by the Cell Cycle-regulated Protein Kinase MELK and Involvement of Splicing Factor NIPP1," *J Biol Chem.*, vol. 279(10), pp. 8642-8647 (Mar. 5, 2004, Epub Dec. 29, 2003).
Geneseq Accession No. ABB04768, 1 page (Mar. 13, 2002).
Geneseq Accession No. ADE38347, 1 page (Jan. 29, 2004).
U.S. Appl. No. 13/168,720, 206 pages, filed Jun. 24, 2011.
U.S. Appl. No. 13/574,774, which is a U.S. National Stage of PCT/JP2011/000352, 83 pages, filed Jan. 24, 2011.
U.S. Appl. No. 13/536,327, filed Jun. 28, 2012, 204 pgs.
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Falk, et al., "Allele-specific motifs revealed by sequencing of self-peptides eluted from MHC molecules," *Nature*, vol. 351(6324), pp. 290-296 (May 23, 1991).
Hoffmann, et al., "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Kubo, et al., "Definition of Specific Peptide Motifs for Four Major HLA-A Alleles," *J Immunol.*, vol. 152(8), pp. 3913-3924 (Apr. 15, 1994).
Rammensee, et al., "MHC ligands and peptide motifs: first listing," *Immunogenetics*, vol. 41(4), pp. 178-228 (1995).
Zaremba, et al., "Identification of an Enhancer Agonist Cytotoxic T Lymphocytes Peptide from Human Carcinoembryonic Antigen," *Cancer Res.*, vol. 57(20), pp. 4570-4577 (Oct. 15, 1997).
Gil, et al., "Cloning and expression of a cDNA encoding a novel protein serine/threonine kinase predominantly expressed in hematopoietic cells," *Gene*, vol. 195(2), pp. 295-301 (Aug. 22, 1997).
Gil, et al., "MPK38 expression is upregulated in immature T cells activated by concanavalin A" *Immunol Lett.*, vol. 64(2-3), pp. 79-83 (Dec. 1998).

\* cited by examiner

Fig. 2a-f

Fig. 2g-i
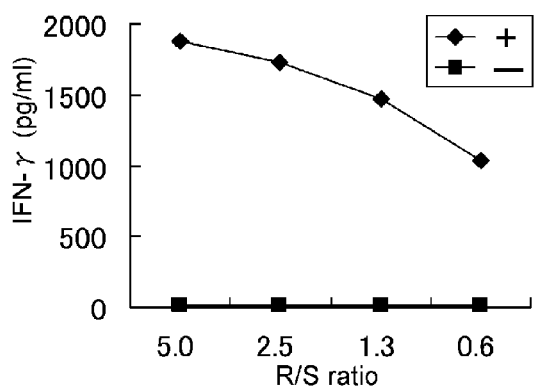
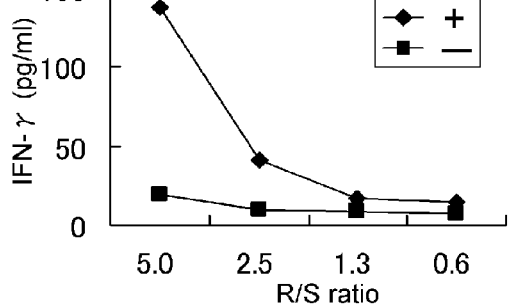
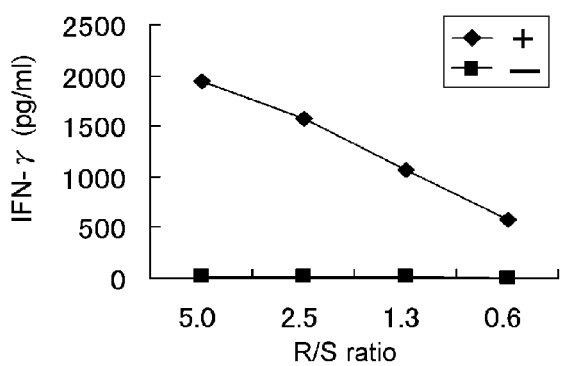
Fig. 3
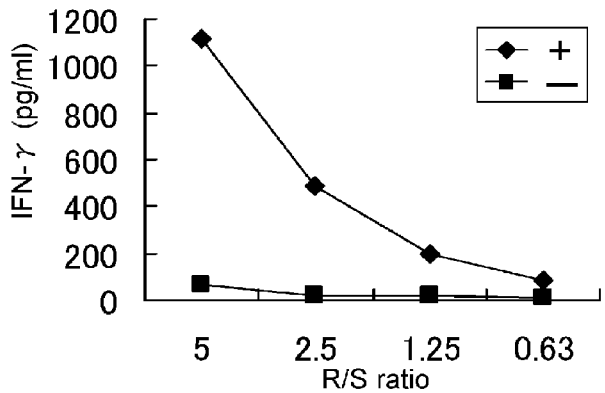

Fig. 4
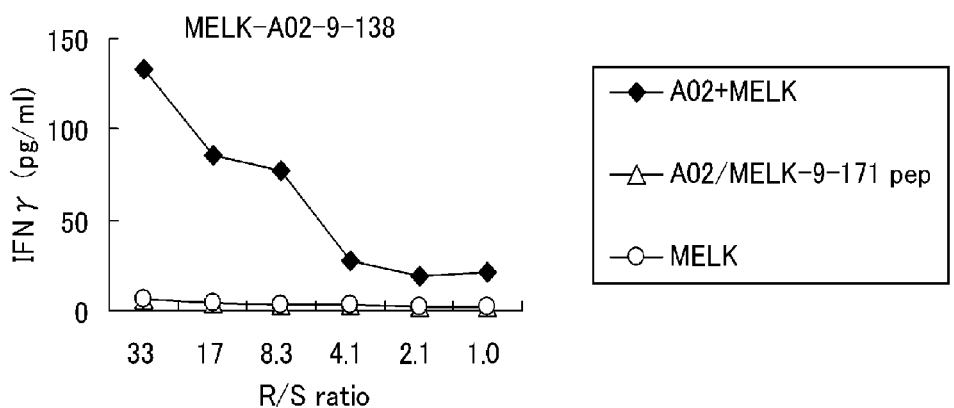
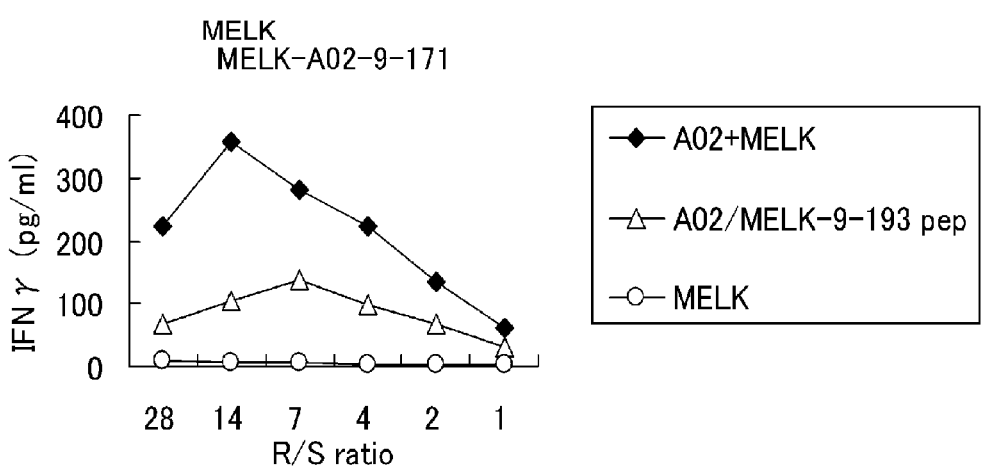

SEQUENCE LISTING

<160> NUMBER OF SEQ ID NOS: 94

<210> SEQ ID NO 1
<211> LENGTH: 9
<212> TYPE: PRT
<213> ORGANISM: Artificial
<220> FEATURE:
<223> OTHER INFORMATION: An artificially synthesized peptide

```
<400> SEQUENCE: 1

Leu Tyr Val Leu Met Cys Gly Phe Leu
1               5

<210> SEQ ID NO 2
<211> LENGTH: 9
<212> TYPE: PRT
<213> ORGANISM: Artificial
<220> FEATURE:
<223> OTHER INFORMATION: An artificially synthesized peptide

<400> SEQUENCE: 2

Asp Tyr Ile Ile Ser Gln Asp Arg Leu
1               5

<210> SEQ ID NO 3
<211> LENGTH: 9
<212> TYPE: PRT
<213> ORGANISM: Artificial
<220> FEATURE:
<223> OTHER INFORMATION: An artificially synthesized peptide

<400> SEQUENCE: 3

His Tyr Asn Val Thr Thr Thr Arg Leu
1               5

<210> SEQ ID NO 4
<211> LENGTH: 9
<212> TYPE: PRT
<213> ORGANISM: Artificial
<220> FEATURE:
<223> OTHER INFORMATION: An artificially synthesized peptide

<400> SEQUENCE: 4

Asp Tyr Asp Trp Cys Glu Asp Asp Leu
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide

<400> SEQUENCE: 5

Lys Tyr Tyr Glu Leu His Glu Thr Ile
1               5

<210> SEQ ID NO 6
<211> LENGTH: 9
<212> TYPE: PRT
<213> ORGANISM: Artificial
<220> FEATURE:
<223> OTHER INFORMATION: An artificially synthesized peptide

<400> SEQUENCE: 6

Glu Tyr Cys Pro Gly Gly Glu Leu Phe
1               5

<210> SEQ ID NO 7
<211> LENGTH: 9
<212> TYPE: PRT
<213> ORGANISM: Artificial
<220> FEATURE:
<223> OTHER INFORMATION: An artificially synthesized peptide

<400> SEQUENCE: 7
```

```
Val Tyr Lys Arg Leu Val Glu Asp Ile
1               5
```

<210> SEQ ID NO 8
<211> LENGTH: 9
<212> TYPE: PRT
<213> ORGANISM: Artificial
<220> FEATURE:
<223> OTHER INFORMATION: An artificially synthesized peptide

<400> SEQUENCE: 8

```
Gln Phe Glu Leu Glu Val Cys Gln Leu
1               5
```

<210> SEQ ID NO 9
<211> LENGTH: 9
<212> TYPE: PRT
<213> ORGANISM: Artificial
<220> FEATURE:
<223> OTHER INFORMATION: An artificially synthesized peptide

<400> SEQUENCE: 9

```
Asp Phe Val Gln Lys Gly Tyr Thr Leu
1               5
```

<210> SEQ ID NO 10
<211> LENGTH: 9
<212> TYPE: PRT
<213> ORGANISM: Artificial
<220> FEATURE:
<223> OTHER INFORMATION: An artificially synthesized peptide

<400> SEQUENCE: 10

```
Val Phe Gly Ser Leu Glu Arg Gly Leu
1               5
```

<210> SEQ ID NO 11
<211> LENGTH: 9
<212> TYPE: PRT
<213> ORGANISM: Artificial
<220> FEATURE:
<223> OTHER INFORMATION: An artificially synthesized peptide

<400> SEQUENCE: 11

```
Arg Leu Val Asn Pro Asp Gln Leu Leu
1               5
```

<210> SEQ ID NO 12
<211> LENGTH: 9
<212> TYPE: PRT
<213> ORGANISM: Artificial
<220> FEATURE:
<223> OTHER INFORMATION: An artificially synthesized peptide

<400> SEQUENCE: 12

```
Asp Phe Gly Lys Val Thr Met Gln Phe
1               5
```

<210> SEQ ID NO 13
<211> LENGTH: 9
<212> TYPE: PRT
<213> ORGANISM: Artificial
<220> FEATURE:
<223> OTHER INFORMATION: An artificially synthesized peptide

<400> SEQUENCE: 13

```
Lys Gly Ala Lys Val Phe Gly Ser Leu
1               5
```

```
<210> SEQ ID NO 14
<211> LENGTH: 9
<212> TYPE: PRT
<213> ORGANISM: Artificial
<220> FEATURE:
<223> OTHER INFORMATION: An artificially synthesized peptide

<400> SEQUENCE: 14

Arg Gly Lys Pro Val Arg Leu Arg Leu
1               5

<210> SEQ ID NO 15
<211> LENGTH: 9
<212> TYPE: PRT
<213> ORGANISM: Artificial
<220> FEATURE:
<223> OTHER INFORMATION: An artificially synthesized peptide

<400> SEQUENCE: 15

Lys Asn Gln His Lys Arg Glu Ile Leu
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide

<400> SEQUENCE: 16

Lys Trp Leu Ser Pro Ser Ser Ile Leu
1               5

<210> SEQ ID NO 17
<211> LENGTH: 9
<212> TYPE: PRT
<213> ORGANISM: Artificial
<220> FEATURE:
<223> OTHER INFORMATION: An artificially synthesized peptide

<400> SEQUENCE: 17

Lys Tyr Trp Thr Glu Ser Asn Gly Val
1               5

<210> SEQ ID NO 18
<211> LENGTH: 9
<212> TYPE: PRT
<213> ORGANISM: Artificial
<220> FEATURE:
<223> OTHER INFORMATION: An artificially synthesized peptide

<400> SEQUENCE: 18

Arg Cys Arg Ser Val Glu Leu Asp Leu
1               5

<210> SEQ ID NO 19
<211> LENGTH: 9
<212> TYPE: PRT
<213> ORGANISM: Artificial
<220> FEATURE:
<223> OTHER INFORMATION: An artificially synthesized peptide

<400> SEQUENCE: 19

Lys Leu Lys Leu Ile Asp Phe Gly Leu
1               5
```

```
<210> SEQ ID NO 20
<211> LENGTH: 9
<212> TYPE: PRT
<213> ORGANISM: Artificial
<220> FEATURE:
<223> OTHER INFORMATION: An artificially synthesized peptide

<400> SEQUENCE: 20

Leu Leu Asn Glu Ile Met Ser Ile Leu
1               5

<210> SEQ ID NO 21
<211> LENGTH: 9
<212> TYPE: PRT
<213> ORGANISM: Artificial
<220> FEATURE:
<223> OTHER INFORMATION: An artificially synthesized peptide

<400> SEQUENCE: 21

Thr Ala Asn Lys Ile Phe Met Val Leu
1               5

<210> SEQ ID NO 22
<211> LENGTH: 9
<212> TYPE: PRT
<213> ORGANISM: Artificial
<220> FEATURE:
<223> OTHER INFORMATION: An artificially synthesized peptide

<400> SEQUENCE: 22

Lys Tyr Asp Val Pro Lys Trp Leu Ser
1               5

<210> SEQ ID NO 23
<211> LENGTH: 10
<212> TYPE: PRT
<213> ORGANISM: Artificial
<220> FEATURE:
<223> OTHER INFORMATION: An artificially synthesized peptide

<400> SEQUENCE: 23

Val Tyr Lys Arg Leu Val Glu Asp Ile Leu
1               5                   10

<210> SEQ ID NO 24
<211> LENGTH: 10
<212> TYPE: PRT
<213> ORGANISM: Artificial
<220> FEATURE:
<223> OTHER INFORMATION: An artificially synthesized peptide

<400> SEQUENCE: 24

Gln Tyr Asp His Leu Thr Ala Thr Tyr Leu
1               5                   10

<210> SEQ ID NO 25
<211> LENGTH: 10
<212> TYPE: PRT
<213> ORGANISM: Artificial
<220> FEATURE:
<223> OTHER INFORMATION: An artificially synthesized peptide

<400> SEQUENCE: 25

Glu Tyr His Lys Leu Lys Leu Ile Asp Phe
1               5                   10

<210> SEQ ID NO 26
<211> LENGTH: 10
```

```
<212> TYPE: PRT
<213> ORGANISM: Artificial
<220> FEATURE:
<223> OTHER INFORMATION: An artificially synthesized peptide

<400> SEQUENCE: 26

Leu Phe Asp Glu Tyr His Lys Leu Lys Leu
1               5                   10

<210> SEQ ID NO 27
<211> LENGTH: 10
<212> TYPE: PRT
<213> ORGANISM: Artificial
<220> FEATURE:
<223> OTHER INFORMATION: An artificially synthesized peptide

<400> SEQUENCE: 27

Arg Gly Leu Asp Lys Val Ile Thr Val Leu
1               5                   10

<210> SEQ ID NO 28
<211> LENGTH: 10
<212> TYPE: PRT
<213> ORGANISM: Artificial
<220> FEATURE:
<223> OTHER INFORMATION: An artificially synthesized peptide

<400> SEQUENCE: 28

Lys Trp Leu Ser Pro Ser Ser Ile Leu Leu
1               5                   10

<210> SEQ ID NO 29
<211> LENGTH: 10
<212> TYPE: PRT
<213> ORGANISM: Artificial
<220> FEATURE:
<223> OTHER INFORMATION: An artificially synthesized peptide

<400> SEQUENCE: 29

Lys Thr Glu Ile Glu Ala Leu Lys Asn Leu
1               5                   10

<210> SEQ ID NO 30
<211> LENGTH: 10
<212> TYPE: PRT
<213> ORGANISM: Artificial
<220> FEATURE:
<223> OTHER INFORMATION: An artificially synthesized peptide

<400> SEQUENCE: 30

Arg Asn Asn Arg Gln Thr Met Glu Asp Leu
1               5                   10

<210> SEQ ID NO 31
<211> LENGTH: 10
<212> TYPE: PRT
<213> ORGANISM: Artificial
<220> FEATURE:
<223> OTHER INFORMATION: An artificially synthesized peptide

<400> SEQUENCE: 31

Arg Gly Lys Tyr Asp Val Pro Lys Trp Leu
1               5                   10

<210> SEQ ID NO 32
<211> LENGTH: 10
<212> TYPE: PRT
<213> ORGANISM: Artificial
```

```
<220> FEATURE:
<223> OTHER INFORMATION: An artificially synthesized peptide

<400> SEQUENCE: 32

Lys Gly Asp Ala Trp Val Tyr Lys Arg Leu
1               5                   10

<210> SEQ ID NO 33
<211> LENGTH: 10
<212> TYPE: PRT
<213> ORGANISM: Artificial
<220> FEATURE:
<223> OTHER INFORMATION: An artificially synthesized peptide

<400> SEQUENCE: 33

Asp Tyr Asn Tyr Pro Val Glu Trp Gln Ser
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide

<400> SEQUENCE: 34

Arg Tyr Thr Thr Pro Ser Lys Ala Arg Asn
1               5                   10

<210> SEQ ID NO 35
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 35

Leu Leu Leu Gln Gln Met Leu Gln Val
1               5

<210> SEQ ID NO 36
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 36

Leu Leu Phe Asp Glu Tyr His Lys Leu
1               5

<210> SEQ ID NO 37
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 37

Ile Met Gln Asp Tyr Asn Tyr Pro Val
1               5

<210> SEQ ID NO 38
<211> LENGTH: 9
<212> TYPE: PRT
<213> ORGANISM: Artificial Sequence
<220> FEATURE:
<223> OTHER INFORMATION: An artificially synthesized peptide
```

```
<400> SEQUENCE: 38

Arg Leu Ser Glu Glu Glu Thr Arg Val
1               5

<210> SEQ ID NO 39
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 39

Lys Leu Ile Asp Phe Gly Leu Cys Ala
1               5

<210> SEQ ID NO 40
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 40

Phe Leu Pro Phe Asp Asp Asp Asn Val
1               5

<210> SEQ ID NO 41
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 41

Leu Leu Asn Glu Ile Met Ser Ile Leu
1               5

<210> SEQ ID NO 42
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 42

Lys Ile Met Arg Gly Lys Tyr Asp Val
1               5

<210> SEQ ID NO 43
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 43

Gln Ile Val Ser Ala Val Ala Tyr Val
1               5

<210> SEQ ID NO 44
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 44
```

Trp Gln Tyr Asp His Leu Thr Ala Thr
1               5

<210> SEQ ID NO 45
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 45

Trp Leu Ser Pro Ser Ser Ile Leu Leu
1               5

<210> SEQ ID NO 46
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 46

Trp Ser Met Gly Ile Leu Leu Tyr Val
1               5

<210> SEQ ID NO 47
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 47

Gln Leu Leu Asn Glu Ile Met Ser Ile
1               5

<210> SEQ ID NO 48
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 48

Tyr Leu Leu Leu Leu Ala Lys Lys Ala
1               5

<210> SEQ ID NO 49
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 49

Ser Leu Trp Gln Tyr Asp His Leu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 50

Lys Leu His Tyr Asn Val Thr Thr Thr

<210> SEQ ID NO 51
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 51

Asn Leu Leu Asn His Pro Trp Ile Met
1               5

<210> SEQ ID NO 52
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 52

Lys Ile Phe Met Val Leu Glu Tyr Cys
1               5

<210> SEQ ID NO 53
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 53

Ile Leu Thr Gly Glu Met Val Ala Ile
1               5

<210> SEQ ID NO 54
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 54

Thr Leu Gly Ser Asp Leu Pro Arg Ile
1               5

<210> SEQ ID NO 55
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 55

Val Thr Met Gln Phe Glu Leu Glu Val
1               5

<210> SEQ ID NO 56
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 56

Phe Ile His Leu Asp Asp Asp Cys Val
1               5

```
<210> SEQ ID NO 57
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 57

Ser Leu Ala Tyr Ala Ala Pro Glu Leu
1               5

<210> SEQ ID NO 58
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 58

Arg Leu Val Asn Pro Asp Gln Leu Leu
1               5

<210> SEQ ID NO 59
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 59

Asn Val Tyr Thr Pro Lys Ser Ala Val
1               5

<210> SEQ ID NO 60
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 60

Gln Leu Tyr His Val Leu Glu Thr Ala
1               5

<210> SEQ ID NO 61
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 61

Ser Leu Thr Pro Ala Leu Cys Arg Thr
1               5

<210> SEQ ID NO 62
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 62

Arg Gly Leu Asp Lys Val Ile Thr Val
1               5

<210> SEQ ID NO 63
```

```
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 63

Lys Leu Lys Leu Ile Asp Phe Gly Leu
1               5

<210> SEQ ID NO 64
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 64

Ser Met Gly Ile Leu Leu Tyr Val Leu
1               5

<210> SEQ ID NO 65
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 65

Ile Leu Thr Thr Pro Asn Arg Tyr Thr
1               5

<210> SEQ ID NO 66
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 66

Ser Ile Leu Leu Leu Gln Gln Met Leu
1               5

<210> SEQ ID NO 67
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 67

Gln Thr Met Glu Asp Leu Ile Ser Leu
1               5

<210> SEQ ID NO 68
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 68

Ile Leu Leu Leu Gln Gln Met Leu Gln Val
1               5                   10

<210> SEQ ID NO 69
<211> LENGTH: 10
<212> TYPE: PRT
```

```
<213> ORGANISM: Artificial Sequence
<220> FEATURE:
<223> OTHER INFORMATION: An artificially synthesized peptide

<400> SEQUENCE: 69

Phe Met Phe Pro Glu Pro Lys Thr Pro Val
1               5                   10

<210> SEQ ID NO 70
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 70

Ile Leu Pro Lys Lys His Val Asp Phe Val
1               5                   10

<210> SEQ ID NO 71
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 71

Trp Leu Ser Pro Ser Ser Ile Leu Leu Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 72

Trp Ile Met Gln Asp Tyr Asn Tyr Pro Val
1               5                   10

<210> SEQ ID NO 73
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 73

Met Gln Phe Glu Leu Glu Val Cys Gln Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 74

Asn Leu Leu Phe Asp Glu Tyr His Lys Leu
1               5                   10

<210> SEQ ID NO 75
<211> LENGTH: 10
<212> TYPE: PRT
<213> ORGANISM: Artificial Sequence
<220> FEATURE:
```

```
<223> OTHER INFORMATION: An artificially synthesized peptide

<400> SEQUENCE: 75

Arg Gln Ile Val Ser Ala Val Ala Tyr Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 76

Val Val Phe Arg Gln Ile Val Ser Ala Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 77

Ile Met Ser Ile Leu Pro Lys Lys His Val
1               5                   10

<210> SEQ ID NO 78
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 78

Leu Leu Tyr Val Leu Met Cys Gly Phe Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 79

Lys Val Thr Met Gln Phe Glu Leu Glu Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 80

Gln Leu Leu Asn Glu Ile Met Ser Ile Leu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: An artificially synthesized peptide
```

```
<400> SEQUENCE: 81

Arg Leu Val Glu Asp Ile Leu Ser Ser Cys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 82

Ser Leu Trp Gln Tyr Asp His Leu Thr Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 83

Leu Glu Thr Ala Asn Lys Ile Phe Met Val
1               5                   10

<210> SEQ ID NO 84
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 84

Gln Leu Gln Lys Pro Asp Val Val Gly Ile
1               5                   10

<210> SEQ ID NO 85
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 85

Arg Leu Ser Glu Glu Glu Thr Arg Val Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 86

Ala Leu Cys Arg Thr Pro Ala Asn Lys Leu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 87
```

Trp Gln Ser Lys Asn Pro Phe Ile His Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 88

Thr Ile Gly Thr Gly Gly Phe Ala Lys Val
1               5                   10

<210> SEQ ID NO 89
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 89

Met Leu Gln Val Asp Pro Lys Lys Arg Ile
1               5                   10

<210> SEQ ID NO 90
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 90

Val Glu Trp Gln Ser Lys Asn Pro Phe Ile
1               5                   10

<210> SEQ ID NO 91
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 91

Trp Val Tyr Lys Arg Leu Val Glu Asp Ile
1               5                   10

<210> SEQ ID NO 92
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 92

Ile Leu Thr Thr Pro Asn Arg Tyr Thr Thr
1               5                   10

<210> SEQ ID NO 93
<211> LENGTH: 2501
<212> TYPE: DNA
<213> ORGANISM: Homo sapiens
<220> FEATURE:
<221> NAME/KEY: CDS
<222> LOCATION: (139)..(2094)

<400> SEQUENCE: 93
cgaaaagatt cttaggaacg ccgtaccagc cgcgtctctc aggacagcag gcccctgtcc      60

-continued

```
ttctgtcggg cgccgctcag ccgtgccctc cgcccctcag gttcttttc taattccaaa    120 taaacttgca agaggact atg aaa gat tat gat gaa ctt ctc aaa tat tat    171
                    Met Lys Asp Tyr Asp Glu Leu Leu Lys Tyr Tyr
                      1               5                   10 gaa tta cat gaa act att ggg aca ggt ggc ttt gca aag gtc aaa ctt    219
Glu Leu His Glu Thr Ile Gly Thr Gly Gly Phe Ala Lys Val Lys Leu
            15                  20                  25 gcc tgc cat atc ctt act gga gag atg gta gct ata aaa tcc atg gat    267
Ala Cys His Ile Leu Thr Gly Glu Met Val Ala Ile Lys Ile Met Asp
        30                  35                  40 aaa aac aca cta ggg agt gat ttg ccc cgg atc aaa acg gag att gag    315
Lys Asn Thr Leu Gly Ser Asp Leu Pro Arg Ile Lys Thr Glu Ile Glu
 45                  50                  55 gcc ttg aag aac ctg aga cat cag cat ata tgt caa ctc tac cat gtg    363
Ala Leu Lys Asn Leu Arg His Gln His Ile Cys Gln Leu Tyr His Val
 60                  65                  70                  75 cta gag aca gcc aac aaa ata ttc atg gtt ctt gag tac tgc cct gga    411
Leu Glu Thr Ala Asn Lys Ile Phe Met Val Leu Glu Tyr Cys Pro Gly
             80                  85                  90 gga gag ctg ttt gac tat ata att tcc cag gat cgc ctg tca gaa gag    459
Gly Glu Leu Phe Asp Tyr Ile Ile Ser Gln Asp Arg Leu Ser Glu Glu
             95                  100                 105 gag acc cgg gtt gtc ttc cgt cag ata gta tct gct gtt gct tat gtg    507
Glu Thr Arg Val Val Phe Arg Gln Ile Val Ser Ala Val Ala Tyr Val
        110                 115                 120 cac agc cag ggc tat gct cac agg gac ctc aag cca gaa aat ttg ctg    555
His Ser Gln Gly Tyr Ala His Arg Asp Leu Lys Pro Glu Asn Leu Leu
        125                 130                 135 ttt gat gaa tat cat aaa tta aag ctg att gac ttt ggt ctc tgt gca    603
Phe Asp Glu Tyr His Lys Leu Lys Leu Ile Asp Phe Gly Leu Cys Ala
140                 145                 150                 155 aaa ccc aag ggt aac aag gat tac cat cta cag aca tgc tgt ggg agt    651
Lys Pro Lys Gly Asn Lys Asp Tyr His Leu Gln Thr Cys Cys Gly Ser
                160                 165                 170 ctg gct tat gca gca cct gag tta ata caa ggc aaa tca tat ctt gga    699
Leu Ala Tyr Ala Ala Pro Glu Leu Ile Gln Gly Lys Ser Tyr Leu Gly
            175                 180                 185 tca gag gca gat gtt tgg agc atg ggc ata ctg tta tat gtt ctt atg    747
Ser Glu Ala Asp Val Trp Ser Met Gly Ile Leu Leu Tyr Val Leu Met
            190                 195                 200 tgt gga ttt cta cca ttt gat gat gat aat gta atg gct tta tac aag    795
Cys Gly Phe Leu Pro Phe Asp Asp Asp Asn Val Met Ala Leu Tyr Lys
        205                 210                 215 aag att atg aga gga aaa tat gat gtt ccc aag tgg ctc tct ccc agt    843
Lys Ile Met Arg Gly Lys Tyr Asp Val Pro Lys Trp Leu Ser Pro Ser
220                 225                 230                 235 agc att ctg ctt ctt caa caa atg ctg cag gtg gac cca aag aaa cgg    891
Ser Ile Leu Leu Leu Gln Gln Met Leu Gln Val Asp Pro Lys Lys Arg
                240                 245                 250 att tct atg aaa aat cta ttg aac cat ccc tgg atc atg caa gat tac    939
Ile Ser Met Lys Asn Leu Leu Asn His Pro Trp Ile Met Gln Asp Tyr
            255                 260                 265 aac tat cct gtt gag tgg caa agc aag aat cct ttt att cac ctc gat    987
Asn Tyr Pro Val Glu Trp Gln Ser Lys Asn Pro Phe Ile His Leu Asp
            270                 275                 280 gat gat tgc gta aca gaa ctt tct gta cat cac aga aac aac agg caa   1035
Asp Asp Cys Val Thr Glu Leu Ser Val His His Arg Asn Asn Arg Gln
        285                 290                 295 aca atg gag gat tta att tca ctg tgg cag tat gat cac ctc acg gct   1083
```

-continued

```
Thr Met Glu Asp Leu Ile Ser Leu Trp Gln Tyr Asp His Leu Thr Ala
300             305                 310                 315 acc tat ctt ctg ctt cta gcc aag aag gct cgg gga aaa cca gtt cgt    1131
Thr Tyr Leu Leu Leu Leu Ala Lys Lys Ala Arg Gly Lys Pro Val Arg
            320                 325                 330 tta agg ctt tct tct ttc tcc tgt gga caa gcc agt gct acc cca ttc    1179
Leu Arg Leu Ser Ser Phe Ser Cys Gly Gln Ala Ser Ala Thr Pro Phe
                335                 340                 345 aca gac atc aag tca aat aat tgg agt ctg gaa gat gtg acc gca agt    1227
Thr Asp Ile Lys Ser Asn Asn Trp Ser Leu Glu Asp Val Thr Ala Ser
            350                 355                 360 gat aaa aat tat gtg gcg gga tta ata gac tat gat tgg tgt gaa gat    1275
Asp Lys Asn Tyr Val Ala Gly Leu Ile Asp Tyr Asp Trp Cys Glu Asp
365                 370                 375 gat tta tca aca ggt gct gct act ccc cga aca tca cag ttt acc aag    1323
Asp Leu Ser Thr Gly Ala Ala Thr Pro Arg Thr Ser Gln Phe Thr Lys
380                 385                 390                 395 tac tgg aca gaa tca aat ggg gtg gaa tct aaa tca tta act cca gcc    1371
Tyr Trp Thr Glu Ser Asn Gly Val Glu Ser Lys Ser Leu Thr Pro Ala
                400                 405                 410 tta tgc aga aca cct gca aat aaa tta aag aac aaa gaa aat gta tat    1419
Leu Cys Arg Thr Pro Ala Asn Lys Leu Lys Asn Lys Glu Asn Val Tyr
            415                 420                 425 act cct aag tct gct gta aag aat gaa gag tac ttt atg ttt cct gag    1467
Thr Pro Lys Ser Ala Val Lys Asn Glu Glu Tyr Phe Met Phe Pro Glu
            430                 435                 440 cca aag act cca gtt aat aag aac cag cat aag aga gaa ata ctc act    1515
Pro Lys Thr Pro Val Asn Lys Asn Gln His Lys Arg Glu Ile Leu Thr
445                 450                 455 acg cca aat cgt tac act aca ccc tca aaa gct aga aac cag tgc ctg    1563
Thr Pro Asn Arg Tyr Thr Thr Pro Ser Lys Ala Arg Asn Gln Cys Leu
460                 465                 470                 475 aaa gaa act cca att aaa ata cca gta aat tca aca gga aca gac aag    1611
Lys Glu Thr Pro Ile Lys Ile Pro Val Asn Ser Thr Gly Thr Asp Lys
                480                 485                 490 tta atg aca ggt gtc att agc cct gag agg cgg tgc cgc tca gtg gaa    1659
Leu Met Thr Gly Val Ile Ser Pro Glu Arg Arg Cys Arg Ser Val Glu
            495                 500                 505 ttg gat ctc aac caa gca cat atg gag gag act cca aaa aga aag gga    1707
Leu Asp Leu Asn Gln Ala His Met Glu Glu Thr Pro Lys Arg Lys Gly
            510                 515                 520 gcc aaa gtg ttt ggg agc ctt gaa agg ggg ttg gat aag gtt atc act    1755
Ala Lys Val Phe Gly Ser Leu Glu Arg Gly Leu Asp Lys Val Ile Thr
525                 530                 535 gtg ctc acc agg agc aaa agg aag ggt tct gcc aga gac ggg ccc aga    1803
Val Leu Thr Arg Ser Lys Arg Lys Gly Ser Ala Arg Asp Gly Pro Arg
540                 545                 550                 555 aga cta aag ctt cac tat aat gtg act aca act aga tta gtg aat cca    1851
Arg Leu Lys Leu His Tyr Asn Val Thr Thr Thr Arg Leu Val Asn Pro
                560                 565                 570 gat caa ctg ttg aat gaa ata atg tct att ctt cca aag aag cat gtt    1899
Asp Gln Leu Leu Asn Glu Ile Met Ser Ile Leu Pro Lys Lys His Val
            575                 580                 585 gac ttt gta caa aag ggt tat aca ctg aag tgt caa aca cag tca gat    1947
Asp Phe Val Gln Lys Gly Tyr Thr Leu Lys Cys Gln Thr Gln Ser Asp
            590                 595                 600 ttt ggg aaa gtg aca atg caa ttt gaa tta gaa gtg tgc cag ctt caa    1995
Phe Gly Lys Val Thr Met Gln Phe Glu Leu Glu Val Cys Gln Leu Gln
605                 610                 615 aaa ccc gat gtg gtg ggt atc agg agg cag cgg ctt aag ggc gat gcc    2043
```

```
Lys Pro Asp Val Val Gly Ile Arg Arg Gln Arg Leu Lys Gly Asp Ala
620                 625                 630                 635 tgg gtt tac aaa aga tta gtg gaa gac atc cta tct agc tgc aag gta      2091
Trp Val Tyr Lys Arg Leu Val Glu Asp Ile Leu Ser Ser Cys Lys Val
                640                 645                 650 taa ttgatggatt cttccatcct gccggatgag tgtgggtgtg atacagccta            2144
cataaagact gttatgatcg ctttgatttt aaagttcatt ggaactacca acttgtttct    2204
aaagagctat cttaagacca atatctcttt gttttaaac aaaagatatt attttgtgta     2264
tgaatctaaa tcaagcccat ctgtcattat gttactgtct ttttaatca gtgttttg        2324 tatattaata attgttgact ttcttagatt cacttccata tgtgaatgta agctcttaac    2384
tatgtctctt tgtaatgtgt aatttctttc tgaaataaaa ccatttgtga atataaaaaa    2444
aaaaaaaaaa aaaaaaaaaa aaaaaaaaaa aaaaaaaaaa aaaaaaaaaa aaaaaaa       2501

<210> SEQ ID NO 94
<211> LENGTH: 651
<212> TYPE: PRT
<213> ORGANISM: Homo sapiens

<400> SEQUENCE: 94

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
    50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270
```

```
Trp Gln Ser Lys Asn Pro Phe Ile His Leu Asp Asp Cys Val Thr
        275                 280                 285
Glu Leu Ser Val His His Arg Asn Asn Arg Gln Thr Met Glu Asp Leu
290                 295                 300
Ile Ser Leu Trp Gln Tyr Asp His Leu Thr Ala Thr Tyr Leu Leu Leu
305                 310                 315                 320
Leu Ala Lys Lys Ala Arg Gly Lys Pro Val Arg Leu Arg Leu Ser Ser
                325                 330                 335
Phe Ser Cys Gly Gln Ala Ser Ala Thr Pro Phe Thr Asp Ile Lys Ser
                340                 345                 350
Asn Asn Trp Ser Leu Glu Asp Val Thr Ala Ser Asp Lys Asn Tyr Val
            355                 360                 365
Ala Gly Leu Ile Asp Tyr Asp Trp Cys Glu Asp Leu Ser Thr Gly
        370                 375                 380
Ala Ala Thr Pro Arg Thr Ser Gln Phe Thr Lys Tyr Trp Thr Glu Ser
385                 390                 395                 400
Asn Gly Val Glu Ser Lys Ser Leu Thr Pro Ala Leu Cys Arg Thr Pro
                405                 410                 415
Ala Asn Lys Leu Lys Asn Lys Glu Asn Val Tyr Thr Pro Lys Ser Ala
                420                 425                 430
Val Lys Asn Glu Glu Tyr Phe Met Phe Pro Glu Pro Lys Thr Pro Val
            435                 440                 445
Asn Lys Asn Gln His Lys Arg Glu Ile Leu Thr Thr Pro Asn Arg Tyr
            450                 455                 460
Thr Thr Pro Ser Lys Ala Arg Asn Gln Cys Leu Lys Glu Thr Pro Ile
465                 470                 475                 480
Lys Ile Pro Val Asn Ser Thr Gly Thr Asp Lys Leu Met Thr Gly Val
                485                 490                 495
Ile Ser Pro Glu Arg Arg Cys Arg Ser Val Glu Leu Asp Leu Asn Gln
                500                 505                 510
Ala His Met Glu Glu Thr Pro Lys Arg Lys Gly Ala Lys Val Phe Gly
            515                 520                 525
Ser Leu Glu Arg Gly Leu Asp Lys Val Ile Thr Val Leu Thr Arg Ser
            530                 535                 540
Lys Arg Lys Gly Ser Ala Arg Asp Gly Pro Arg Arg Leu Lys Leu His
545                 550                 555                 560
Tyr Asn Val Thr Thr Thr Arg Leu Val Asn Pro Asp Gln Leu Leu Asn
                565                 570                 575
Glu Ile Met Ser Ile Leu Pro Lys Lys His Val Asp Phe Val Gln Lys
            580                 585                 590
Gly Tyr Thr Leu Lys Cys Gln Thr Gln Ser Asp Phe Gly Lys Val Thr
            595                 600                 605
Met Gln Phe Glu Leu Glu Val Cys Gln Leu Gln Lys Pro Asp Val Val
        610                 615                 620
Gly Ile Arg Arg Gln Arg Leu Lys Gly Asp Ala Trp Val Tyr Lys Arg
625                 630                 635                 640
Leu Val Glu Asp Ile Leu Ser Ser Cys Lys Val
                645                 650
```

MELK EPITOPE PEPTIDES AND VACCINES CONTAINING THE SAME

CROSS-REFERENCE TO RELATED APPLICATIONS

The present application is a U.S. National Stage Application of PCT/JP2009/003630, filed Jul. 30, 2009, which claims the benefit of U.S. Provisional Application No. 61/085,663, filed on Aug. 1, 2008, the entire contents of which are incorporated by reference herein in their entirety.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive CTLs recognize epitope peptides derived from the tumor-associated antigens (TAAs) found on major histocompatibility complex (MHC) class I molecules, and then kill the tumor cells. Since the discovery of the melanoma antigen (MAGE) family as the first example of TAAs, many other TAAs have been discovered, primarily through immunological approaches (Boon T, Int J Cancer 1993 May 8, 54(2): 177-80; Boon T & van der Bruggen P, J Exp Med 1996 Mar. 1, 183(3): 725-9). Some of these TAAs are currently undergoing of clinical development as immunotherapeutic targets.

Identification of new TAAs, capable of inducing potent and specific anti-tumor immune responses, warrants further development and clinical application of peptide vaccination strategies for various types of cancer (Harris C C, J Natl Cancer Inst 1996 Oct. 16, 88(20): 1442-55; Butterfield L H et al., Cancer Res 1999 July 1, 59(13): 3134-42; Vissers J L et al., Cancer Res 1999 Nov. 1, 59(21): 5554-9; van der Burg S H et al., J Immunol 1996 May 1, 156(9): 3308-14; Tanaka F et al., Cancer Res 1997 Oct. 15, 57(20): 4465-8; Fujie T et al., Int J Cancer 1999 Jan. 18, 80(2): 169-72; Kikuchi M et al., Int J Cancer 1999 May 5, 81(3): 459-66; Oiso M et al., Int J Cancer 1999 May 5, 81(3): 387-94). To date, there have been several reports of clinical trials using these tumor-associated antigen derived peptides. Unfortunately, only a low objective response rate has been observed in these cancer vaccine trials so far (Belli F et al., J Clin Oncol 2002 Oct. 15, 20(20): 4169-80; Coulie P G et al., Immunol Rev 2002 October, 188: 33-42; Rosenberg S A et al., Nat Med 2004 September, 10(9): 909-15).

Recently, algorithms for predicting HLA class I-binding peptide sequences have been developed (Journal of Immunological Methods, (1995), Vol. 185, pp. 181-190, J. Immunol., (1994), Vol. 152, pp. 163-175, protein science, (2000), Vol. 9, pp. 1838-1846). However, it is difficult to estimate if a predicted epitope peptide can be processed naturally in the target cells and expressed on the target cell surface with HLA molecule. Moreover, the algorithms, for example BIMAS (world wide web bimas.dcrt.nih.gov/cgi-bin/molbio/ken_parker_comboform) (Parker K C, et al., (1994) J. Immunol.; 152(1): 163-75; Kuzushima K, et al., (2001) Blood; 98(6):1872-81.)) can suggest less than rigorous HLA molecule-binding peptides (Bachinsky M M, et. al., Cancer Immun. 2005 Mar. 22; 5:6.). Thus, identifying epitope peptides remains challenging and difficult.

MELK, maternal embryonic leucine zipper kinase, was previously identified as a new member of the snf1/AMPK serine-threonine kinase family that is involved in mammalian embryonic development (Heyer B S et al., Dev Dyn. 1999 August 215(4):344-51). The gene was shown to play an important role in stem cell renewal (Nakano I et al., J Cell Biol. 2005 Aug. 1, 170(3):413-27), cell-cycle progression (Blot J et al., Dev Biol. 2002 Jan. 15, 241(2):327-38; Seong H A et al., Biochem J. 2002 Feb. 1, 361(Pt 3):597-604) and pre-mRNA splicing (Vulsteke V et al., J Biol Chem. 2004 Mar. 5, 279(10):8642-7. Epub 2003 Dec. 29). In addition, through gene expression profile analysis using a genome-wide cDNA microarray containing 23,040 genes, MELK was recently shown to be up-regulated in breast cancer (Lin M L et al., Breast Cancer Res. 2007; 9 (1):R17, WO2006/016525, WO2008/023841). In fact, MELK is up-regulated in several cancer cells, for example lung, bladder, lymphoma and cervical cancer cells (See WO2004/031413, WO2007/013665, and WO2006/085684, the disclosures of which are incorporated by reference herein). Northern blot analysis on multiple human tissues and cancer cell lines demonstrated that MELK was over-expressed at a significantly high level in a great majority of breast cancers and cell lines, but was not expressed in normal vital organs (heart, liver, lung and kidney) (WO2006/016525). Furthermore, suppression of MELK expression by siRNA was shown to significantly inhibit growth of human breast cancer cells. Accordingly, MELK is considered to be a suitable target for cancer immunotherapy and epitope peptides derived therefrom may be expected to serve as cancer immunotherapeutics effective in the treatment of a wide array of cancer types.

SUMMARY OF INVENTION

The present invention is based in part on the discovery of suitable targets of immunotherapy. Because TAAs are generally perceived by the immune system as "self" and therefore often have no innate immunogenicity, the discovery of appropriate targets is of extreme importance. Recognizing that MELK has been identified as up-regulated in cancer tissues of breast cancer, bladder cancer, cervical cancer, cholangio-cellular carcinoma, chronic myeloid leukemia (CML), colorectal cancer, endometriosis, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCC), the present invention targets this maternal embryonic leucine zipper kinase (MELK) protein (SEQ ID NO: 94) encoded by the gene of GenBank Accession No. NM_014791 (SEQ ID NO: 93) for further analysis. In particular, MELK gene products containing epitope peptides that elicit CTLs specific to the corresponding molecules were selected for study. Peripheral blood mononuclear cells (PBMCs) obtained from a healthy donor were stimulated using HLA-A*2402 or HLA-A*0201 binding candidate peptides derived from MELK. CTLs that specifically recognize HLA-A24 or HLA-A02 positive target cells pulsed with the respective candidate peptides were established, and HLA-A24 or HLA-A02 restricted epitope peptides that can induce potent and specific immune responses against MELK expressed on the surface of tumor cells were identified. These results demonstrate that MELK is strongly immunogenic and the epitopes thereof are effective targets for tumor immunotherapy.

Accordingly, it is an object of the present invention to provide peptides having CTL inducibility as well as an amino acid sequence selected from the group of SEQ ID NOs: 14, 21, 23, 27, 36, 46, 57, 60 and 62. In addition, the present invention con-templates modified peptides, having an amino acid sequence of SEQ ID NOs: 14, 21, 23, 27, 36, 46, 57, 60 or 62, wherein one, two or more amino acids are substituted, deleted, incorporated, and/or added, so long as the modified peptides retain the original CTL inducibility.

When administered to a subject, the present peptides are presented on the surface of antigen-expressing cells and then induce CTLs targeting the respective peptides. Therefore, it is an object of the present invention to provide antigen-presenting cells which present any of the present peptides, as well as methods for inducing antigen-presenting cells. An anti-tumor immune response is induced by the administration of the present MELK polypeptides or polynucleotide encoding the polypeptides, as well as exosomes and antigen-presenting cells which present the MELK polypeptides. Therefore, it is yet another object of the present invention to provide pharmaceutical agents or compositions containing the polypeptides or polynucleotides encoding them, as well as the exosomes and antigen-presenting cells as their active ingredients. The pharmaceutical agents of the present invention find use as vaccines.

It is a further object of the present invention to provide methods for the treatment and/or prophylaxis of (i.e., preventing) cancers (tumors), and/or prevention of post-operative recurrence thereof, as well as methods for inducing CTLs, methods for inducing an immune response against tumor-associated endothelia and also anti-tumor immunity, which methods include the step of administering the MELK polypeptides, polynucleotides encoding MELK polypeptides, exosomes or the antigen-presenting cells presenting MELK polypeptides or the pharmaceutical agents of the invention. In addition, the CTLs of the invention also find use as vaccines against cancer. Examples of the cancer include, but are not limited to breast cancer, bladder cancer, cervical cancer, cholangiocellular carcinomas, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC.

It is to be understood that both the foregoing summary of the invention and the following detailed description are of exemplified embodiments, and not restrictive of the invention or other alternate embodiments of the invention.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 3 depicts the IFN-gamma production of the CTL clone established by limiting dilution from the CTL line stimulated with SEQ ID NO: 27. The results depicted herein demonstrate that the CTL clone established by stimulation with SEQ ID NO: 27 showed potent IFN-gamma production as compared with the control. In the figure, "+" indicates that the target cells were pulsed with SEQ ID NO: 27 and "−" indicates that the target cells had not been pulsed with any peptides.

FIG. 4 is composed of line graphs (a) and (b) depicting specific CTL activity of the CTL clones established with MELK-A02-9-138 (SEQ ID NO:36) (a) or MELK-A02-9-171 (SEQ ID NO: 57) (b) against target cells that exogenously express MELK and HLA-A*0201. The target cells were prepared by co-transfecting COS7 cells with the full length of both MELK and HLA-A*0201 molecule gene (-closed diamond-), and the control target cells were prepared by transfecting COS7 cells with HLA-A*0201 molecule gene and pulsing with an inappropriate peptide that is different from the peptides with which the CTL clones were established (-open triangle-), or transfecting COS7 cells with MELK gene (-open circle-). The CTL clone established with MELK-A02-9-138 (SEQ ID NO: 36) (a) and MELK-A02-9-171 (SEQ ID NO: 57) (b) showed potent IFN-gamma production against COS7 cells transfected with both MELK and HLA-A*0201 (-closed diamond-) as compared with the controls (-open triangle-, -open circle-).

DESCRIPTION OF EMBODIMENTS

Figure 1:
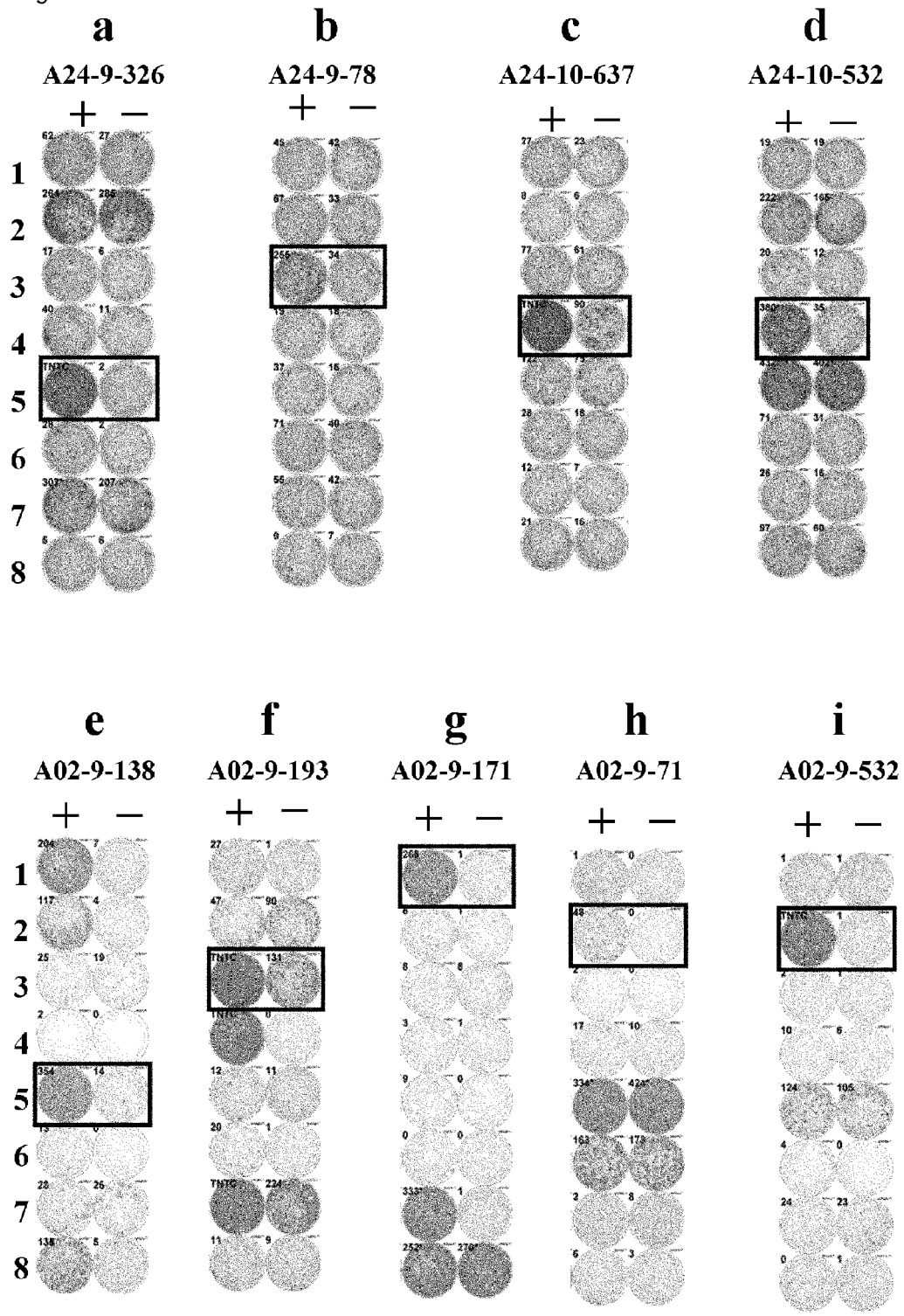
FIG. 1 includes a series of photographs, (a)-(i) depicting the results of IFN-gamma ELISPOT assay on CTLs that were induced with peptides derived from MELK. The CTLs in well number #5 stimulated with MELK-A24-9-326 (SEQ ID NO: 14) (a), #3 with MELK-A24-9-78 (SEQ ID NO: 21) (b), #4 with MELK-A24-10-637 (SEQ ID NO: 23) (c), #4 with MELK-A24-10-532 (SEQ ID NO: 27) (d), #5 with MELK-A02-9-138 (SEQ ID NO: 36) (e), #3 with MELK-A02-9-193 (SEQ ID NO: 46) (f), #1 with MELK-A02-9-171 (SEQ ID NO: 57) (g), #2 with MELK-A02-9-71 (SEQ ID NO: 60), (h) and #2 with MELK-A02-9-532 (SEQ ID NO: 62) (i) showed potent IFN-gamma production as compared with the control, respectively. The cells in the wells denoted with a rectangular box were expanded to establish CTL lines. In the figures, "+" indicates that the target cells in the well were pulsed with the appropriate peptide, and "−" indicates that the target cells had not been pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated, are similarly to the amino acids referred to by their commonly accepted single-letter codes.

Unless otherwise defined, the term "cancer" refers to the cancers over-expressing the MELK gene, examples of which include, but are not limited to, breast cancer, bladder cancer, cervical cancer, cholangiocellular carcinoma, chronic myeloid leukemia (CML), colorectal cancer, endometriosis, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCC)s.

Unless otherwise defined, the term "cytotoxic T lymphocyte", "cytotoxic T cell" and "CTL" are used interchangeably herein and, unless otherwise specifically indicated, refer to a sub-group of T lymphocytes that are capable of recognizing non-self cells (e.g., tumor cells, virus-infected cells) and inducing the death of such cells.

Unless otherwise defined, all technical and scientific terms used herein have the same meaning as commonly understood by one of ordinary skill in the art to which this invention belongs.

II. Peptides

To demonstrate that peptides derived from MELK function as an antigen recognized by cytotoxic T lymphocytes (CTLs), peptides derived from MELK (SEQ ID NO: 93) were analyzed to determine whether they were antigen epitopes restricted by HLA-A24 or HLA-A02 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A24 or HLA-A02 binding peptides derived from MELK were identified based on their binding affinities to HLA-A24 or HLA-A02. After in vitro stimulation of T-cells by dendritic cells (DCs) loaded with these peptides, CTLs were successfully established using the following peptides:

```
MELK-A24-9-326,     (SEQ ID NO: 14)
MELK-A24-9-78,      (SEQ ID NO: 21)
MELK-A24-10-637,    (SEQ ID NO: 23)
MELK-A24-10-532,    (SEQ ID NO: 27)
MELK-A02-9-138,     (SEQ ID NO: 36)
MELK-A02-9-193,     (SEQ ID NO: 46)
MELK-A02-9-171,     (SEQ ID NO: 57)
MELK-A02-9-71,      (SEQ ID NO: 60)
and
MELK-A02- 9-532,    (SEQ ID NO: 62)
```

These established CTLs show potent specific CTL activity against target cells pulsed with respective peptides. These results herein demonstrate that MELK is an antigen recognized by CTL and that the peptides may be epitope peptides of MELK restricted by HLA-A24 or HLA-A02.

Since the MELK gene is over expressed in most cancer tissues, such as breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC, it is a good target for immunotherapy. Thus, the present invention provides nonapeptides (peptides consisting of nine amino acid residues) and decapeptides (peptides consisting of ten amino acid residues) corresponding to CTL-recognized epitopes of MELK. Particularly preferred examples of nonapeptides and decapeptides of the present invention include those peptides consisting of the amino acid sequence selected from among SEQ ID NOs: 14, 21, 23, 27, 36, 46, 57, 60 and 62.

Generally, software programs presently available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in the references to Parker K C et al., J Immunol 1994 Jan. 1, 152(1): 163-75; and Kuzushima K et al., Blood 2001, 98(6): 1872-81. The methods for determining binding affinity is described, for example, in; Journal of Immunological Methods, 1995, 185: 181-190; Protein Science, 2000, 9: 1838-1846. Thus, the present invention encompasses peptides of MELK which bind with HLA antigens identified using such known programs.

The nonapeptides and decapeptides of the present invention can be flanked with additional amino acid residues so long as the resulting peptide retains its CTL inducibility. Such peptides having CTL inducibility are typically less than about 40 amino acids, often less than about 20 amino acids, usually less than about 15 amino acids. The particular amino acid sequences flanking the nonapeptide and decapeptides of the present invention (e.g., peptides consisting of the amino acid sequence selected from among SEQ ID NOs: 14, 21, 23, 27, 36, 46, 57, 60 and 62 is not limited and can be composed of any kind of amino acids so long as it does not impair the CTL inducibility of the original peptide. Thus, the present invention also provides peptides having CTL inducibility and including the amino acid sequence selected from among SEQ ID NOs: 14, 21, 23, 27, 36, 46, 57, 60 and 62.

In general, the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NOs: 14, 21, 23, 27, 36, 46, 57, 60 and 62 wherein one, two or even more amino acids are added, inserted, deleted and/or substituted.

Those skilled in the art recognize that individual modification to an amino acid sequence which alters a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the modified peptide retains the CTL inducibility of the original peptide. Furthermore, modified peptides should not exclude CTL inducible peptides of polymorphic variants, interspecies homologues, and alleles of MELK.

To retain the requisite CTL inducibility one can modify (insert, delete, add, and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

Homology analysis of preferred peptides of the present invention, MELK-A24-9-326 (SEQ ID NO: 14), MELK-A24-9-78 (SEQ ID NO: 21), MELK-A24-10-637 (SEQ ID NO: 23), MELK-A24-10-532 (SEQ ID NO: 27), MELK-A02-9-138 (SEQ ID NO: 36), MELK-A02-9-193 (SEQ ID NO: 46), MELK-A02-9-171 (SEQ ID NO: 57), MELK-A02-9-71 (SEQ ID NO: 60) and MELK-A02-9-532 (SEQ ID NO: 62) confirmed that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in tumor patients against MELK on cancer cells, such as breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC.

When used in the context of immunotherapy, peptides of the present invention should be presented on the surface of a cell or exosome, preferably as a complex with an HLA antigen. Therefore, one is preferable to select peptides that not only induce CTLs but also possess high binding affinity to the HLA antigen. To that end, the peptides can be modified by substitution, insertion, deletion, and/or addition of the amino acid residues to yield a modified peptide having improved binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the present invention. For example, it may be desirable to substitute the second amino acid from the N-terminus with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from among SEQ ID NO: 14, SEQ ID NO: 21, SEQ ID NO: 23 and SEQ ID NO: 27 wherein the second amino acid from the N-terminus of the amino acid sequence of the SEQ ID NOs is substituted with phenylalanine, tyrosine, methionine, or tryptophan, and/or wherein the C-terminus of the amino acid sequence of the SEQ ID NOs is substituted with phenylalanine, leucine, isoleucine, tryptophan, or methionine are encompassed by the present invention. On the other hand, peptides possessing high HLA-A02 binding affinity have their second amino acid from the N-terminus substituted with leucine or methionine, and/or the amino acid at C-terminus substituted with valine or leucine. Thus, peptides having the amino acid sequences selected from among SEQ ID NO: 36, SEQ ID NO: 46, SEQ ID NO: 57, SEQ ID NO: 60 and SEQ ID NO: 62 wherein the second amino acid from the N-terminus is substituted with leucine or methionine, and/or wherein the C-terminus is substituted with valine or leucine are encompassed by the present invention. Substitutions can be introduced not only at the terminal amino acids but also at the position of potential TCR recognition of peptides. Several studies have demonstrated that amino acid substitutions in a peptide can be equal to or better than the original, for example CAP1, $p53_{(264-272)}$, $Her-2/neu_{(369-377)}$ or $gp 100_{(209-217)}$ (Zaremba et al. Cancer Res. 57, 4570-4577, 1997, T. K. Hoffmann et al. J. Immunol. (2002) February 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one to two amino acids to the N and/or C-terminus of the described peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic lymphocytes (CTLs) when presented on antigen-presenting cells. Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing antigen-presenting cells carrying human MHC antigens (for example, B-lymphocytes, macrophages, and dendritic cells (DCs)) by stimulating with the peptides, mixing the induced antigen-presenting cells with CD8-positive cells, and then measuring the IFN-gamma produced and released by CTL against the target cells. Preferably, antigen-presenting cells are DCs derived from human peripheral blood mononuclear leukocytes. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}Cr$ and such, and cytotoxic activity can be calculated from radioactivity released from the target cells. Alternatively, CTL inducibility can be assessed by measuring IFN-gamma produced and released by CTL in the presence of antigen-presenting cells (APCs) that carry immobilized peptides, and visualizing the inhibition zone on the media using anti-IFN-gamma monoclonal antibodies.

As a result of assessing the CTL inducibility of the peptides as described above, it was discovered that those peptides predicted having high binding affinity to an HLA antigen did not necessarily have high CTL inducibility. However, of those peptides identified and assessed, nonapeptides or decapeptides having an amino acid sequence selected from among SEQ ID NOs: 14, 21, 23, 27, 36, 46, 57, 60 and 62 were found to exhibit particularly high CTL inducibility. Thus, these peptides are exemplified as preferred embodiments of the present invention.

In addition to the above-described modifications, the peptides of the present invention can also be linked to other substances, so long as the resulting linked peptide retains the requisite CTL inducibility of the original peptide. Examples of suitable substances include, but are not limited to: peptides, lipids, sugar and sugar chains, acetyl groups, natural and synthetic polymers, etc. The peptides can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept can also be adapted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Further, the peptides of the present invention may be linked to other peptides via spacers or linkers. Examples of other peptides include, but are not limited to, CTL inducible peptides derived from other TAAs. Alternatively, two or more peptides of the present invention may be linked via spacers or linkers. The peptides linked via spacers or linkers may be the same or different each other. Spacers or linkers are not specifically limited, but are preferably peptides, more preferably peptides having one or more cleavage sites which are capable of being cleaved by enzymes such as peptidases, proteases and proteasomes. Examples of linkers or spacers include, but are not limited to: AAY (P. M. Daftarian et al., J Trans Med 2007, 5:26), AAA, NKRK (R. P. M. Sutmuller et al., J Immunol. 2000, 165: 7308-7315) or, one to several lysine residues (S. Ota et al., Can Res. 62, 1471-1476, K. S. Kawamura et al., J Immunol. 2002, 168: 5709-5715). The peptides of the present invention encompass those peptides linked to other peptides via spacers or linkers.

The peptides of the present invention may be existed on the surface of a cell carrying human MHC antigens (e.g. antigen presenting cell) or an exosome as complexes in combination with MHC molecules and then induce CTLs. The cells and the exosomes can be prepared by well-known methods in the art, for example, the cells may be prepared by contacting with the peptides of the present invention, and the exosomes may be prepared by collecting an exosome-containing fraction from the cells contacted with the peptides of the present invention (see, e.g., Japanese Patent Application Kohyo Publications Nos. Hei 11-510507 and WO99/03499). The peptide of the present invention encompass those peptides existed on the surface of a cell or an exosome as complexes in combination with MHC molecules.

Herein, the peptides of the present invention can also be described as "MELK peptide(s)" or "MELK polypeptide(s)".

III. Preparation of MELK Peptides

The peptides of the present invention can be prepared using well known techniques. For example, the peptides can be prepared synthetically, using recombinant DNA technology or chemical synthesis. Peptide of the invention can be synthesized individually or as longer polypeptides composed of two or more peptides. The peptides can then be isolated i.e., purified or isolated so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. Polynucleotides

The present invention also provides a polynucleotide which encodes any of the aforementioned peptides of the present invention. These include polynucleotides derived from the natural occurring MELK gene (GenBank Accession No. NM_014791 (SEQ ID NO: 93)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention, with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

Vectors containing the polynucleotide of the present invention and host cells harboring the vectors are also included in the present invention.

V. Exosomes

The present invention further provides intracellular vesicles called exosomes, which present complexes formed between the peptides of this invention and HLA antigens on their surface. Exosomes can be prepared, for example by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens contained in the complexes must match that of the subject requiring treatment and/or prevention. For example, in the Japanese population, HLA-A24, particularly HLA-A2402, is prevalent and therefore would be appropriate for treatment of a Japanese patient. The use of the A24 type or the A02 type that is highly expressed among the Japanese and Caucasian is favorable for obtaining effective results, and subtypes such as A2402 or A0201 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion and/or addition of 1, 2, or several amino acids can be performed based on the amino acid sequence of the naturally occurring MELK partial peptide.

When using an exosome including the A24 type HLA antigen, the peptides having the amino acid sequences selected from among SEQ ID NOs: 14, 21, 23 and 27 are useful. On the other hand, when using an exosome including A02 type HLA antigen, the peptides having the sequences selected from among SEQ ID NO: 36, 46, 57, 60 and 62 are preferred.

VI. Antigen-Presenting Cells (APCs)

The present invention also provides isolated APCs that present complexes formed between HLA antigens and the peptides of this invention on its surface. The APCs that are obtained by contacting the peptides of this invention, or introducing the nucleotides encoding the peptides of this invention in an expressible form can be derived from patients who are subject to treatment and/or prevention, and can be administered as vaccines by themselves or in combination with other drugs including the peptides of this invention, exosomes, or cytotoxic T cells.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, an APC can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. The phrase "inducing APC" includes contacting (stimulating) a cell with the peptides of this invention, or nucleotides encoding the peptides of this invention to present complexes formed between HLA antigens and the peptides of this invention on cell's surface. After introducing the peptides of this invention to the APCs to allow the APCs to present the peptides, the APCs can be administered to the subject as a vaccine. For example, the ex vivo administration can include the steps of:

a: collecting APCs from a first subject,
b: contacting with the APCs of step a, with the peptide and
c: administering the peptide-loaded APCs to a second subject.

The first subject and the second subject can be the same individual, or may be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method or the process includes the step of admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

According to an aspect of the present invention, the APCs of the present invention have a high level of CTL inducibility. In the term of "high level of CTL inducibility", the high level is relative to the level of that by APCs contacted with no peptide or peptides which can not induce the CTL. Such APCs having a high level of CTL inducibility can be prepared by a method which includes the step of transferring genes containing polynucleotides that encode the peptides of this invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. Cytoxic T Cells (CTLS)

A cytotoxic T cell induced against any of the peptides of the present invention strengthens the immune response targeting tumor-associated endothelia in vivo and thus can be used as vaccines, in a fashion similar to the peptides per se. Thus, the present invention also provides isolated cytotoxic T cells that are specifically induced or activated by any of the present peptides.

Such cytotoxic T cells can be obtained by (1) administering the peptide of the present invention to a subject and then collecting cytotoxic T cells from the subject, or (2) contacting (stimulating) subject-derived APCs and CD8-positive cells, or peripheral blood mononuclear leukocytes in vitro with the peptides of the present invention and then isolating cytotoxic T cells.

The cytotoxic T cells, which have been induced by stimulation with APCs that present the peptides of this invention, can be derived from patients who are subject to treatment and/or prevention, and can be administered by themselves or in combination with other drugs including the peptides of this invention or exosomes for the purpose of regulating effects. The obtained cytotoxic T cells act specifically against target cells presenting the peptides of this invention, or for example, the same peptides used for induction. In the other word, the cytotoxic T cells can recognize (i.e., binding to) a complex formed between a HLA antigen and the peptide of the present invention on a target cell surface with the T cell receptor and then attack the target cell to induce the death of the target cell. The target cells can be cells that endogenously express MELK, or cells that are transfected with the MELK gene; and cells that present a peptide of this invention on the cell surface due to stimulation by the peptide can also serve as targets of activated CTL attack.

VIII. T Cell Receptor (TCR)

The present invention also provides a composition containing nucleic acids sequence encoding polypeptides that are capable of forming a subunit of a T cell receptor (TCR), and methods of using the same. The TCR subunits have the ability to form TCRs that confer specificity to T cells against tumor cells presenting MELK. By using the known methods in the art, the nucleic acid sequence of alpha- and beta-chains of the TCR expressed in the CTL induced with a peptide of the present invention can be identified (WO2007/032255 and Morgan et al., J Immunol, 171, 3288 (2003)). The derivative TCRs can bind to the MELK peptide displaying on the target cells with high avidity, and optionally mediate efficient killing of target cells presenting the MELK peptide in vivo and in vitro.

The nucleic acids sequence encoding the TCR subunits can be incorporated into suitable vectors e.g. retroviral vectors. These vectors are well known in the art. The nucleic acids or the vectors containing them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides that bind to the MELK peptide e.g. SEQ ID NOs: 14, 21, 23, 27, 36, 46, 57, 60 and 62 in the context of HLA-A24 or HLA-A02. The transduced CTLs are capable of homing to cancer cells in vivo, and can be expanded by well known culturing methods in vitro (e.g., Kawakami et al., J Immunol., 142, 3452-3461 (1989)). The T cells of the invention can be used to form an immunogenic composition useful in treating or the prevention of cancer in a patient in need of therapy or protection (WO2006/031221).

IX. Pharmaceutical Agents or Compositions

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors.

Treating and/or the prophylaxis of cancer or tumor, and/or the prevention of post-operative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis includes 10%, 20%, 30% or more reduction, or stable disease.

Since MELK expression is up-regulated in several cancers as compared with normal tissue, the peptides of this invention or polynucleotides encoding such peptides can be used for the treatment and/or for the prophylaxis of cancer or tumor, and/or prevention of postoperative recurrence thereof. Thus, the present invention provides a pharmaceutical agent or composition for treating and/or for the prophylaxis of cancer or tumor, and/or prevention of postoperative recurrence thereof, which includes one or more of the peptides of this invention, or polynucleotides encoding the peptides as an active ingredient. Alternatively, the present peptides can be expressed on the surface of any of the foregoing exosomes or cells, such as APCs for the use as pharmaceutical agents or compositions. In addition, the aforementioned cytotoxic T cells which target any of the peptides of the present invention can also be used as the active ingredient of the present pharmaceutical agents or compositions. In the context of the present invention, the phrase "targeting a peptide" refers to recognizing (i.e., binding to) a complex formed between a HLA antigen and a peptide on a target cell surface with the T cell receptor, and then attacking the target cell to induce the death of the target cell.

In another embodiment, the present invention also provides the use of an active ingredient selected from among:
  (a) a peptide of the present invention,
  (b) a nucleic acid encoding such a peptide as disclosed herein in an expressible form,
  (c) an APC or an exosome presenting a peptide of the present invention on its surface, and
  (d) a cytotoxic T cell of the present invention in manufacturing a pharmaceutical composition or agent for treating cancer or tumor.

Alternatively, the present invention further provides an active ingredient selected from among:
  (a) a peptide of the present invention,
  (b) a nucleic acid encoding such a peptide as disclosed herein in an expressible form,
  (c) an APC or an exosome presenting a peptide of the present invention on its surface, and
  (d) a cytotoxic T cells of the present invention for use in for treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
  (a) a peptide of the present invention,
  (b) a nucleic acid encoding such a peptide as disclosed herein in an expressible form,
  (c) an APC or an exosome presenting a peptide of the present invention on its surface, and
  (d) a cytotoxic T cells of the present invention as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
  (a) a peptide of the present invention,
  (b) a nucleic acid encoding such a peptide as disclosed herein in an expressible form,
  (c) an APC or an exosome presenting a peptide of the present invention on its surface, and
  (d) a cytotoxic T cells of the present invention.

Alternatively, the pharmaceutical composition or agent of the present invention may be used for either or both the prophylaxis of cancer or tumor and prevention of post-operative recurrence thereof.

The present pharmaceutical agents or compositions find use as a vaccine. In the context of the present invention, the phrase "vaccine" (also referred to as an "immunogenic composition") refers to a substance that has the function to induce anti-tumor immunity upon inoculation into animals.

The pharmaceutical agents or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, polypeptides having an amino acid sequence selected from among SEQ ID NOs: 14, 21, 23 and 27 or polypeptides having an amino acid sequence selected from among SEQ ID NOs: 36, 46, 57, 60 and 62 have been found to be HLA-A24 or HLA-A02 restricted epitope peptides or candidates, respectively, that can induce potent and specific immune response. Therefore, the present pharmaceutical agents or compositions which include any of these polypeptides having the amino acid sequences selected from among of SEQ ID NOs: 14, 21, 23 and 27 are particularly suited for the administration to subjects whose HLA antigen is HLA-A24. On the one hand, the present pharmaceutical agents or compositions which contain any of these polypeptides having the amino acid sequences of SEQ ID NOs: 36, 46, 57, 60 and 62 are particularly suited for the administration to subjects whose HLA antigen is HLA-A02. The same applies to pharmaceutical agents which include polynucleotides encoding any of these polypeptides.

Cancers or tumors to be treated by the pharmaceutical agents or compositions of the present invention are not limited and include all kinds of cancers or tumors wherein MELK is involved, including for example, bladder cancer, breast cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC.

The present pharmaceutical agents or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents or compositions of this invention can include other agents conventional in the art having regard to the type of formulation in question.

In one embodiment of the present invention, the present pharmaceutical agents or compositions can be included in articles of manufacture and kits containing materials useful for treating the pathological conditions of the disease to be treated, e.g, cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for ad-ministration.

(1) Pharmaceutical Agents or Compositions Containing the Peptides as the Active Ingredient The peptides of this invention can be administered directly as a pharmaceutical agent or composition, or if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared as a combination, composed of two or more of peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface, which may be obtained by stimulating APCs (e.g., DCs) derived from a subject with the peptides of this invention, may be administered to the subject, and as a result, CTLs are induced in the subject and aggressiveness towards the cancer cells, such as bladder cancer, breast cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC cells, can be increased.

The pharmaceutical agents or compositions for the treatment and/or prevention of cancer or tumor, which include a peptide of this invention as the active ingredient, can also include an adjuvant known to effectively cellular immunity. Alternatively, the pharmaceutical agents or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In some embodiments, the pharmaceutical agents or compositions of the present invention may further include a component which primes CTLs. Lipids have been identified as agents capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTLs responses, *E. coli* lipoproteins, such as tripalmitoyl-S-glycerylcysteinlyseryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Examples of another vector include BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods using the Peptides, Exosomes, APCs AND CTLs

The peptides of the present invention and polynucleotides encoding such peptides can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed below.

(1) Method of Inducing Antigen-Presenting Cells (APCs)

The present invention provides methods of inducing APCs using the peptides of this invention or polynucleotides encoding the peptides. The induction of APCs can be performed as described above in section "VI. Antigen-presenting cells". This invention also provides a method for inducing APCs having a high level of CTL inducibility, the induction of which has been also mentioned under the item of "VI. Antigen-presenting cells", supra.

Preferably, the methods for inducing APCs include at least one step selected from among:

a: contacting APCs with the peptides of the present invention, and b: introducing the polypeptides of the present invention in an expressible form into APCs.

Such methods for inducing APCs are preferably performed in vitro or ex vivo. When the methods performed in vitro or ex vivo, APCs to be induced may be obtained from a subject to be treated or others whose HLA antigens are the same as the subject.

(2) Method of Inducing CTLs

Furthermore, the present invention provides methods for inducing CTLs using the peptides of this invention, polynucleotides encoding the peptides, or exosomes or APCs presenting the peptides.

The present invention also provides methods for inducing CTLs using a polynucleotide encoding a polypeptide that is capable of forming a T cell receptor (TCR) subunit recognizing (i.e., binding to) a complex of the peptides of the present invention and HLA antigens on a cell surface. Preferably, the methods for inducing CTLs include at least one step selected from among:

a: contacting a CD8-positive T cell with an antigen-presenting cell and/or an exosome that presents on its surface a complex of an HLA antigen and a peptide of the present invention, and b: introducing a polynucleotide encoding a polypeptide that is capable of forming a TCR subunit recognizing a complex of a peptide of the present invention and an HLA antigen into a CD8 positive T cell.

When the peptides of the present invention are administered to a subject, CTLs are induced in the body of the subject, and the strength of the immune response targeting the tumor-associated endothelia is enhanced. Alternatively, the peptides and polynucleotides encoding the peptides can be used for an ex vivo therapeutic method, in which subject-derived APCs and CD8-positive cells, or peripheral blood mononuclear leukocytes are contacted (stimulated) with the peptides of this invention in vitro, and after inducing CTLs, the activated CTL cells are returned to the subject. For example, the method can include steps of:

a: collecting APCs from subject, b: contacting with the APCs of step a, with the peptide, c: mixing the APCs of step b with $CD^{8+}$ T cells, and co-culturing for inducing CTLs, and d: collecting $CD^{8+}$ T cells from the co-culture of step c.

Alternatively, according to the present invention, use of the peptides of this invention for manufacturing a pharmaceutical agent or composition inducing CTLs is provided. In addition, the present invention provides a method or process for manufacturing a pharmaceutical agent or composition inducing CTLs, wherein the method includes the step of admixing or formulating the peptide of the present invention with a pharmaceutically acceptable carrier. Further, the present invention also provides the peptide of the present invention for inducing CTLs. The $CD^{8+}$ T cells having cytotoxic activity obtained by step d can be administered to the subject as a vaccine. The APCs to be mixed with the $CD^{8+}$ T cells in above step c can also be prepared by transferring genes coding for the present peptides into the APCs as detailed above in section "VI. Antigen-presenting cells"; but are not limited thereto. Accordingly, any APCs or exosomes which effectively presents the present peptides to the T cells can be used for the present method.

The following examples are presented to illustrate the present invention and to assist one of ordinary skill in making and using the same. The examples are not intended in any way to otherwise limit the scope of the invention.

EXAMPLES

Materials and Methods

Cell Lines

A24 lymphoblastoid cell line (A24LCL) was established by transformation with Epstein-bar virus into HLA-A24 positive human B lymphocyte. T2 (HLA-A2), human B-lymphoblastoid cell line, and COST were purchased from ATCC.

Candidate Selection of Peptides Derived from MELK 9-mer and 10-mer peptides derived from MELK that bind to HLA-A*2402 and HLA-A*0201 molecules were predicted using binding prediction software "BIMAS" (world wide web-bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). These peptides were synthesized by Sigma (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 July 15, 63(14): 4112-8). Specifically, peripheral blood mononuclear cells (PBMCs) isolated from a normal volunteer (HLA-A*2402 or HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 microgram/ml of each of the synthesized peptides in the presence of 3 microgram/ml of beta2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 microgram/ml for 30 min) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTL was tested against peptide-pulsed A24LCL or T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with 1×10⁴ cells/well of 2 kinds of human B-lymphoblastoid cell lines, 30 ng/ml of anti-CD3 antibody, and 125 U/ml of IL-2 in a total of 150 microliter/well of AIM-V Medium containing 5% AS. 50 microliter/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24LCL or T2 (1×10⁴/well) was prepared as stimulator cells. Cultured cells in 48 wells were used as responder cells. IFN-gamma ELISPOT assay and IFN-gamma ELISA assay were performed under manufacture procedure.

Results

Over Expression in Cancers

The global gene expression profile data obtained from various cancers using cDNA-microarray revealed that MELK (GenBank Accession No. NM_014791; SEQ ID No. 93) expression was elevated. MELK expression was validly elevated in 29 out of 29 bladder cancer, 31 out of 34 breast cancer, 14 out of 15 cervical cancer, 11 out of 11 cholangiocellular carcinoma, 10 out of 13 CML, 12 out of 15 colorectal cancer, 2 out of 2 endometriosis, 19 out of 42 esophagus cancer, 5 out of 6 gastric cancer, 4 out of 4 liver cancer, 11 out of 11 NSCLC, 13 out of 14 lymphoma, 14 out of 18 osteosarcoma, 3 out of 6 ovarian cancer, 2 out of 2 pancreatic cancer, 18 out of 21 prostate cancer, 5 out of 6 renal carcinoma and 15 out of 15 small cell lung cancer as compared with corresponding normal tissue. (Table 1).

TABLE 1

Ratio of cases observed up-regulation of MELK in cancerous tissue as compared with normal corresponding tissue

| Cancer | Ratio |
| --- | --- |
| Bladder Cancer | 29/29 |
| Breast Cancer | 31/34 |
| Cervical Cancer | 14/15 |
| Cholangiocellular Carcinoma | 11/11 |
| CML | 10/13 |
| Colorectal cancer | 12/15 |
| Endometriosis | 2/2 |
| Esophagus cancer | 19/42 |
| Gastric cancer | 5/6 |
| Liver cancer | 4/4 |
| non-small cell lung cancer | 11/11 |
| Lymphoma | 13/14 |
| Osteosarcoma | 14/18 |
| Ovarian cancer | 3/6 |
| Pancreatic cancer | 2/2 |
| Prostate cancer | 18/21 |
| Renal Carcinoma | 5/6 |
| Small cell Lung Cancer | 15/15 |

Prediction of HLA-A24 and HLA-A2 Binding Peptides Derived from MELK

Table 2 shows the HLA-A24 and HLA-A2 binding peptides of MELK in order of highest binding affinity. A total of 34 peptides with potential HLA-A24 binding ability were selected and examined to determine the epitope peptides (Table 2a), and a total of 58 peptides having potential HLA-A2 binding ability were similarly selected and examined to determine the epitope peptides (Table 2b and c).

TABLE 2a

HLA-A24 binding 9 mer and 10 mer peptides derived from MELK

| Start Position | Amino acid sequence | Binding Score | SEQ ID NO. |
| --- | --- | --- | --- |
| 199 | LYVLMCGFL | 300 | 1 |
| 96 | DYIISQDRL | 300 | 2 |
| 560 | HYNVTTTRL | 300 | 3 |
| 373 | DYDWCEDDL | 200 | 4 |
| 9 | KYYELHETI | 144 | 5 |
| 87 | EYCPGGELF | 120 | 6 |
| 637 | VYKRLVEDI | 60 | 7 |
| 610 | QFELEVCQL | 30 | 8 |
| 588 | DFVQKGYTL | 30 | 9 |
| 526 | VFGSLERGL | 24 | 10 |
| 567 | RLVNPDQLL | 14.4 | 11 |
| 603 | DFGKVTMQF | 14 | 12 |
| 522 | KGAKVFGSL | 13.44 | 13 |
| 326 | RGKPVRLRL | 13.44 | 14 |
| 450 | KNQHKREIL | 12 | 15 |
| 230 | KWLSPSSIL | 12 | 16 |
| 395 | KYWTESNGV | 12 | 17 |
| 502 | RCRSVELDL | 11.2 | 18 |
| 145 | KLKLIDFGL | 11.2 | 19 |
| 574 | LLNEIMSIL | 10.08 | 20 |
| 78 | TANKIFMVL | 10.08 | 21 |
| 225 | KYDVPKWLS | 10 | 22 |
| 637 | VYKRLVEDIL | 280 | 23 |
| 309 | QYDHLTATYL | 200 | 24 |
| 142 | EYHKLKLIDF | 100 | 25 |
| 139 | LFDEYHKLKL | 26.4 | 26 |
| 532 | RGLDKVITVL | 20.16 | 27 |
| 230 | KWLSPSSILL | 12 | 28 |
| 55 | KTEIEALKNL | 12 | 29 |
| 295 | RNNRQTMEDL | 12 | 30 |
| 223 | RGKYDVPKWL | 11.2 | 31 |
| 632 | KGDAWVYKRL | 11.2 | 32 |
| 266 | DYNYPVEWQS | 10.5 | 33 |
| 463 | RYTTPSKARN | 10 | 34 |

TABLE 2b

HLA-A2 binding 9 mer peptides derived from MELK

| Start Position | Amino acid sequence | Binding Score | SEQ ID NO. |
|---|---|---|---|
| 238 | LLLQQMLQV | 1006.209 | 35 |
| 138 | LLFDEYHKL | 826.372 | 36 |
| 263 | IMQDYNYPV | 350.117 | 37 |
| 103 | RLSEEETRV | 285.163 | 38 |
| 147 | KLIDFGLCA | 270.905 | 39 |
| 206 | FLPFDDDNV | 156.77 | 40 |
| 574 | LLNEIMSIL | 140.409 | 41 |
| 220 | KIMRGKYDV | 123.846 | 42 |
| 115 | QIVSAVAYV | 120.977 | 43 |
| 308 | WQYDHLTAT | 104.878 | 44 |
| 231 | WLSPSSILL | 98.267 | 45 |
| 193 | WSMGILLYV | 97.752 | 46 |
| 573 | QLLNEIMSI | 88.783 | 47 |
| 317 | YLLLLAKKA | 84.555 | 48 |
| 306 | SLWQYDHLT | 61.852 | 49 |
| 558 | KLHYNVTTT | 59.989 | 50 |
| 256 | NLLNHPWIM | 56.523 | 51 |
| 81 | KIFMVLEYC | 54.833 | 52 |
| 31 | ILTGEMVAI | 40.792 | 53 |
| 46 | TLGSDLPRI | 23.995 | 54 |
| 607 | VTMQFELEV | 23.089 | 55 |
| 279 | FIHLDDDCV | 21.556 | 56 |
| 171 | SLAYAAPEL | 21.362 | 57 |
| 567 | RLVNPDQLL | 21.362 | 58 |
| 425 | NVYTPKSAV | 19.475 | 59 |
| 71 | QLYHVLETA | 17.917 | 60 |
| 407 | SLTPALCRT | 17.14 | 61 |
| 532 | RGLDKVITV | 15.841 | 62 |
| 145 | KLKLIDFGL | 15.178 | 63 |
| 194 | SMGILLYVL | 14.549 | 64 |
| 457 | ILTTPNRYT | 13.935 | 65 |
| 236 | SILLLQQML | 10.868 | 66 |
| 299 | QTMEDLISL | 10.352 | 67 |

TABLE 2c

HLA-A2 binding 10 mer peptides derived from MELK

| Start Position | Amino acid sequence | Binding Score | SEQ ID NO. |
|---|---|---|---|
| 237 | ILLLQQMLQV | 1006.209 | 68 |
| 439 | FMFPEPKTPV | 854.949 | 69 |
| 581 | ILPKKHVDFV | 732.901 | 70 |
| 231 | WLSPSSILLL | 226.014 | 71 |
| 262 | WIMQDYNYPV | 162.769 | 72 |
| 609 | MQFELEVCQL | 128.47 | 73 |
| 137 | NLLFDEYHKL | 118.561 | 74 |
| 114 | RQIVSAVAYV | 89.205 | 75 |
| 111 | VVFRQIVSAV | 88.043 | 76 |
| 578 | IMSILPKKHV | 85.394 | 77 |
| 198 | LLYVLMCGFL | 83.091 | 78 |
| 606 | KVTMQFELEV | 80.941 | 79 |
| 573 | QLLNEIMSIL | 74.536 | 80 |
| 640 | RLVEDILSSC | 46.848 | 81 |
| 306 | SLWQYDHLTA | 41.234 | 82 |
| 76 | LETANKIFMV | 30.67 | 83 |
| 617 | QLQKPDVVGI | 23.995 | 84 |
| 103 | RLSEEETRVV | 23.383 | 85 |
| 411 | ALCRTPANKL | 21.362 | 86 |
| 273 | WQSKNPFIHL | 18.93 | 87 |
| 16 | TIGTGGFAKV | 18.17 | 88 |
| 243 | MLQVDPKKRI | 17.736 | 89 |
| 271 | VEWQSKNPFI | 15.743 | 90 |
| 636 | WVYKRLVEDI | 15.144 | 91 |
| 457 | ILTTPNRYTT | 12.668 | 92 |

Start position indicates the number of amino acid residue from the N-terminal of MELK. Binding score is derived from "BIMAS".

Figure 2:
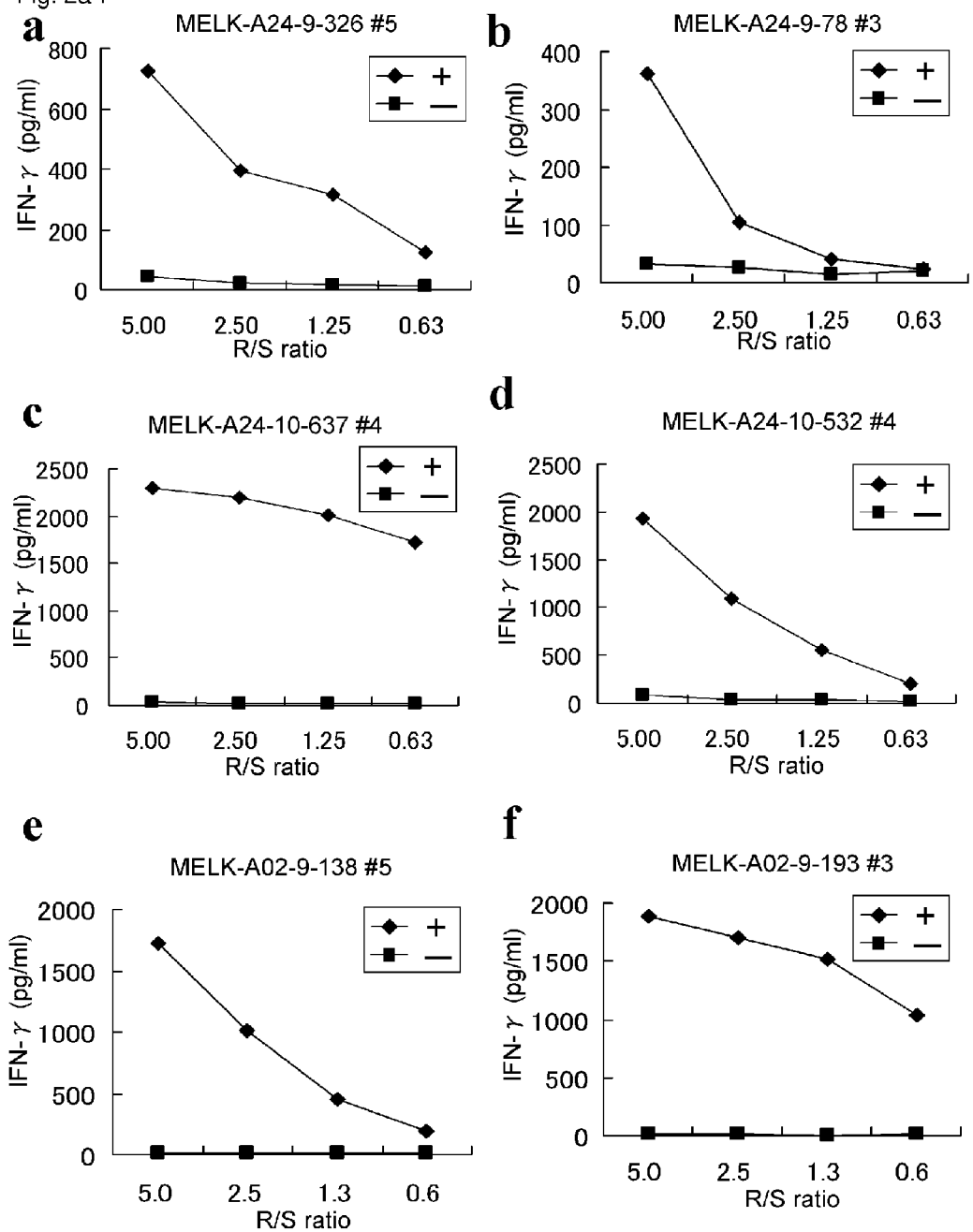
FIG. 2 includes a series of line graphs, (a)-(i), depicting the IFN-gamma production of CTL lines stimulated with SEQ ID NO: 14 (a), SEQ ID NO: 21 (b), SEQ ID NO: 23 (c), SEQ ID NO: 27 (d), SEQ ID NO: 36 (e), SEQ ID NO: 46 (f), SEQ ID NO: 57 (g), SEQ ID NO: 60 (h) and SEQ ID NO: 62 (i) with IFN-gamma ELISA assay. CTL lines established by stimulation with each peptide showed potent IFN-gamma production as compared with the control. In the figures, "+" indicates that the target cells were pulsed with the appropriate peptide and "−" indicates that the target cells had not been pulsed with any peptides.

CTL Induction with the Predicted Peptides from MELK Restricted with HLA-A*2402 or HLA-A*0201 and Establishment for CTL Lines Stimulated with MELK Derived Peptides CTLs for those peptides derived from MELK were generated according to the protocols as described in "Materials and Methods". Peptide specific CTL activity was determined by IFN-gamma ELISPOT assay (FIG. 1a-i). It showed that #5 stimulated with MELK-A24-9-326 (SEQ ID NO: 14) (a), #3 with MELK-A24-9-78 (SEQ ID NO: 21) (b), #4 with MELK-A24-10-637 (SEQ ID NO: 23) (c), #4 with MELK-A24-10-532 (SEQ ID NO: 27) (d), #5 with MELK-A02-9-138 (SEQ ID NO: 36) (e), #3 with MELK-A02-9-193 (SEQ ID NO: 46) (f), #1 with MELK-A02-9-171 (SEQ ID NO: 57) (g), #2 with MELK-A02-9-71 (SEQ ID NO: 60) (h) and #2 with MELK-A02-9-532 (SEQ ID NO: 62) (i) demonstrated potent IFN-gamma production as compared to the control wells. Furthermore, the cells in the positive well number #5 stimulated with SEQ ID NO: 14, #3 with SEQ ID NO: 21, #4 with SEQ ID NO: 23, #4 with SEQ ID NO: 27, #5 with SEQ ID NO: 36, #3 with SEQ ID NO: 46, #1 with SEQ ID NO: 57, #2 with SEQ ID NO: 60 and #2 with SEQ ID NO: 62 were expanded and established CTL lines. CTL activity of those CTL lines was determined by IFN-gamma ELISA assay (FIG. 2a-i). All CTL lines demonstrated potent IFN-gamma production against the target cells pulsed with corresponding peptide as compared to target cells without peptide pulse. On the other hand, no CTL lines could be established by stimulation with other peptides shown in Table 2, despite those peptide had possible binding activity with HLA-A*2402 or HLA-A*0201 (data not shown). Consequently, only nine peptides out of 92 candidate peptide derived from MELK could induce potent CTL lines.

Establishment of CTL Clones Against MELK Specific Peptides

CTL clones were established by limiting dilution from CTL lines as described in "Materials and Methods", and IFN-gamma production from CTL clones against target cells pulsed peptide were determined by IFN-gamma ELISA assay. Potent IFN-gamma productions were determined from CTL clones stimulated with SEQ ID NO: 27 in FIG. 3.

Specific CTL Activity Against Target Cells Presenting the Peptide Endogenously Processed from MELK with HLA-A*0201

The established CTL lines raised against these peptides were examined for their ability to recognize target cells presenting the candidate peptide endogenously processed from MELK with HLA-A*0201 molecule. Specific CTL activity against COS7 cells which transfected with both the full length of MELK and HLA-A*0201 molecule gene (a specific model for the target cells that express MELK and HLA-A*0201 gene) was tested using the CTL lines raised by corresponding peptide as the effecter cells. COS7 cells transfected with either full length of MELK genes or HLA-A* 0201 were prepared as control. In FIG. 4, the CTLs stimulated with SEQ ID NO: 36 (a) and SEQ ID NO: 57 (b) showed potent CTL activity against COS7 cells ex-pressing both MELK and HLA-A02. On the other hand, no significant specific CTL activity was detected against the controls. Thus, these data clearly demonstrate that the peptides having the amino acid sequences of SEQ ID NO: 36 and SEQ ID NO: 57 are naturally presented on the target cells with HLA-A*0201 molecule and are recognized by the CTLs. These results indicated that those two peptides derived from MELK may be available to apply the cancer vaccines for patients with MELK expressing tumors.

Homology Analysis of Antigen Peptides

The CTLs stimulated with MELK-A24-9-326 (SEQ ID NO: 14), MELK-A24-9-78 (SEQ ID NO: 21), MELK-A24-10-637 (SEQ ID NO: 23), MELK-A24-10-532 (SEQ ID NO: 27), MELK-A02-9-138 (SEQ ID NO: 36), MELK-A02-9-193 (SEQ ID NO: 46), MELK-A02-9-171 (SEQ ID NO: 57), MELK-A02-9-71 (SEQ ID NO: 60) and MELK-A02-9-532 (SEQ ID NO: 62) showed significant and specific CTL activity. This result may be due to the fact that the sequences of MELK-A24-9-326 (SEQ ID NO: 14), MELK-A24-9-78 (SEQ ID NO: 21), MELK-A24-10-637 (SEQ ID NO: 23), MELK-A24-10-532 (SEQ ID NO: 27), MELK-A02-9-138 (SEQ ID NO: 36), MELK-A02-9-193 (SEQ ID NO: 46), MELK-A02-9-171 (SEQ ID NO: 57), MELK-A02-9-71 (SEQ ID NO: 60) and MELK-A02-9-532 (SEQ ID NO: 62) are homologous to peptides derived from other molecules that are known to sensitize the human immune system. To exclude this possibility, homology analyses were performed for these peptide sequences using as queries the BLAST algorithm (world wide web.ncbi.nlm.nih.gov/blast/blast.cgi) which revealed no sequence with significant homology. The results of homology analyses indicate that the sequences of MELK-A24-9-326 (SEQ ID NO: 14), MELK-A24-9-78 (SEQ ID NO: 21), MELK-A24-10-637 (SEQ ID NO: 23), MELK-A24-10-532 (SEQ ID NO: 27), MELK-A02-9-138 (SEQ ID NO: 36), MELK-A02-9-193 (SEQ ID NO: 46), MELK-A02-9-171 (SEQ ID NO: 57), MELK-A02-9-71 (SEQ ID NO: 60) and MELK-A02-9-532 (SEQ ID NO: 62) are unique and thus, there is little possibility, to our best knowledge, that these molecules raise unintended immunologic responses to some unrelated molecules.

In conclusion, novel HLA-A24 and HLA-A02 epitope peptides derived from MELK were identified and demonstrated to be applicable for cancer immunotherapy.

INDUSTRIAL APPLICABILITY

The present invention describes new TAAs, particularly those derived from MELK which induce potent and specific anti-tumor immune responses and have applicability to a wide array of cancer types. Such TAAs warrant further development as peptide vaccines against diseases associated with MELK, e.g. cancers such as breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide of less than 15 amino acids, wherein said peptide comprises an amino acid sequence selected from the group consisting of:
   (a) SEQ ID NO: 36; and
   (b) SEQ ID NO: 36, in which 1 or 2 amino acids are substituted, inserted, deleted and/or added, and has cytotoxic T lymphocyte (CTL) inducibility.

2. The peptide as set forth in claim 1, wherein the peptide is a nonapeptide or a decapeptide.

3. The peptide as set forth in claim 1, wherein the peptide has one or both of the following characteristics:
   (a) the second amino acid from the N-terminus of the amino acid sequence of SEQ ID NO: 36 is selected from the group of leucine or methionine, and
   (b) the C-terminal amino acid of the amino acid sequence of SEQ ID NO: 36 is selected from the group of valine or leucine.

4. A composition comprising one or more peptides as set forth in claim 1 as an active ingredient.

5. A method for inducing an antigen-presenting cell with high CTL inducibility, wherein the method comprises the step of contacting an antigen-presenting cell with a peptide as set forth in claim 1.

6. A method for inducing CTL by using a peptide as set forth in claim 1.

7. The method for inducing CTL, wherein said method comprises the step of contacting a CD8-positive T cell with an antigen-presenting cell and/or an exosome which presents a complex formed between a HLA antigen and a peptide as set forth in claim 1 on its surface.

8. An agent for inducing CTL activity against a cell expressing both MELK and HLA-A02, wherein said agent comprises one or more peptides as set forth in claim 1 as an active ingredient.

* * * * *

UNITED STATES PATENT AND TRADEMARK OFFICE
CERTIFICATE OF CORRECTION

| | |
|---|---|
| PATENT NO. | : 8,674,069 B2 |
| APPLICATION NO. | : 13/056598 |
| DATED | : March 18, 2014 |
| INVENTOR(S) | : Tsunoda et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 341 days.

Signed and Sealed this
Eleventh Day of August, 2015

Michelle K. Lee
*Director of the United States Patent and Trademark Office*